United States Patent
Kikuchi et al.

(10) Patent No.: US 6,801,650 B1
(45) Date of Patent: Oct. 5, 2004

(54) MECHANISM AND METHOD FOR CONTROLLING FOCAL POINT POSITION OF UV LIGHT AND APPARATUS AND METHOD FOR INSPECTION

(75) Inventors: Hiroki Kikuchi, Kanagawa (JP); Asahiko Nogami, Tokyo (JP); Masayuki Morita, Saitama (JP)

(73) Assignee: Sony Corporation, Tokyo (JP)

( * ) Notice: Subject to any disclaimer, the term of this patent is extended or adjusted under 35 U.S.C. 154(b) by 770 days.

(21) Appl. No.: 09/661,743

(22) Filed: Sep. 14, 2000

(30) Foreign Application Priority Data

Sep. 14, 1999 (JP) .......................................... P11-261176

(51) Int. Cl.[7] ................................................. G06K 9/00
(52) U.S. Cl. ..................... 382/145; 250/548; 250/201.4; 250/372
(58) Field of Search ....................... 382/145; 250/201.2, 250/201.4, 559.29, 559.39, 559.45, 559.48, 201.8, 203.1, 372, 548; 29/833; 438/16; 356/237.3, 237.5, 239.3

(56) References Cited

U.S. PATENT DOCUMENTS

| | | | | |
|---|---|---|---|---|
| 4,677,301 A | * | 6/1987 | Tanimoto et al. ............ 250/548 |
| 4,815,058 A | * | 3/1989 | Nakamura et al. ........ 369/44.23 |
| 5,532,874 A | * | 7/1996 | Stein ........................... 359/394 |
| 5,576,831 A | * | 11/1996 | Nikoonahad et al. ........ 356/623 |
| 5,880,465 A | * | 3/1999 | Boettner et al. ............. 250/234 |
| 6,034,780 A | * | 3/2000 | Kato ........................... 356/400 |
| 6,061,606 A | * | 5/2000 | Ross ........................... 700/121 |
| 6,172,373 B1 | * | 1/2001 | Hara et al. ................... 250/548 |
| 6,411,377 B1 | * | 6/2002 | Noguchi et al. ......... 356/237.4 |
| 6,541,747 B1 | * | 4/2003 | Kikuchi et al. ........... 250/201.2 |

* cited by examiner

*Primary Examiner*—Samir Ahmed
(74) *Attorney, Agent, or Firm*—Sonnenschein, Nath & Rosenthal LLP

(57) ABSTRACT

A method and apparatus for controlling the focal position of the UV light for auto-focussing the converged UV light, and a method and apparatus and for inspecting a device, such as a semiconductor wafer or liquid crystal using the converged UV light, in which the UV light converged is to be auto-focussed accurately and speedily. The method includes an inspection stage 11 for supporting a semiconductor wafer, an objective lens for UV light 40 or converging a UV laser light for illuminating the laser light converged to the semiconductor wafer, a distance sensor 41 secured to this objective lens for UV light 40 to detect the distance to the semiconductor wafer and a controller for causing movement of the inspection stage 11 in a perpendicular direction. The controller causes the distance between the objective lens for UV light 40 and the semiconductor wafer to coincide with the target distance T based on the distance as detected by the distance sensor 41.

34 Claims, 20 Drawing Sheets

| X COORDINATE (mm) | Y COORDINATE (mm) | FIRST CORRECTION C1 |
|---|---|---|
| 0 | 0 | -0.1 |
| 0 | 0 | -0.1 |
| 0 | 10 | 0 |
| 0 | 15 | 0 |
| . | . | . |
| . | . | . |
| . | . | . |
| 5 | 0 | +0.1 |
| 5 | 5 | +0.1 |
| 5 | 10 | +0.2 |
| 5 | 15 | +0.2 |
| 5 | 20 | +0.2 |
| . | . | . |
| . | . | . |
| . | . | . |
| 50 | 0 | 0 |
| 50 | 5 | 0 |
| 50 | 10 | -0.1 |
| . | . | . |
| . | . | . |
| . | . | . |

FIG.16

MECHANISM AND METHOD FOR CONTROLLING FOCAL POINT POSITION OF UV LIGHT AND APPARATUS AND METHOD FOR INSPECTION

RELATED APPLICATION DATA

The present application claims priority to Japanese Application No. P11-261176 filed Sep. 14, 1999, which application is incorporated herein by reference to the extent permitted by law.

BACKGROUND OF THE INVENTION

1. Field of the Invention

This invention relates to a mechanism and a method for controlling the focal position of the UV light for auto-focussing the converged UV light, and to a method and apparatus for inspecting a device, such as a semiconductor wafer or liquid crystal, using the converged UV light.

2. Description of the Related Art

A semiconductor device is prepared by forming a fine device pattern on a semiconductor wafer. If, in the semiconductor device manufacturing process, contaminants become affixed, patten defects re produced or unusual dimensions are encountered, defects are produced in the device pattern. The semiconductor device, suffering these defects, represents a reject device, leading to lowered yield in the manufacturing process.

For stabilizing the yield in the manufacturing process at a high level, it is necessary to find pattern defects or defects ascribable to unusual dimensions, to locate the reason and to take effective measures for the manufacturing process. By locating the reason of defects to take proper measures for the manufacturing process in order to improve the yield, a new process can be started promptly to realize a high profit with the process.

If a defect is produced in the semiconductor device, the defect is searched, using a microscopic device for semiconductor inspection, to search into the reason of defects to specify the equipment or the process ascribable for the defect based on the searched results. The microscopic device for semiconductor inspection is a device, exemplified by an optical microscope, in which defects on a semiconductor wafer can be enlarged and observed, or the enlarged defect can be imaged to display the image on a monitor. Using this microscopic device for semiconductor inspection, it is possible to discriminate the nature of the defect on the defective device.

Nowadays, the design rule for the semiconductor device is prevalently 0.18 $\mu$m in line width, or even finer, such that the process with the line width of 0.15 $\mu$m or 0.13 $\mu$m is being introduced. In keeping pace with the tendency to this fine design rule in the semiconductor process, fine defects which could be discounted in the past now raise problems, with the size of the defects to be detected being smaller.

Thus, in the conventional microscopic device for semiconductor inspection, the defects are enlarged using a light source for the visible light to observer the enlarged image. For coping with the fine design rule, a proposal has been made for a microscopic device for semiconductor inspection in which the defect is enlarged using the light source for the UV light to observe the enlarged image. By employing the UV light source, high resolution can be achieved to enable finer defects to be observed.

Since the objective lens designed for a light source for visible light does not transmit the UV light, it is necessary with the microscopic device for semiconductor inspection employing the UV light source to use a lens for UV light designed to demonstrate imaging performance optimum for the wavelength of the UV light.

However, the objective lens for the UV light, which assures high multiplication factor, the depth of focus becomes extremely short. For example, if the numerical aperture NA is 0.9, the multiplication factor is 100 and the wavelength of the UV light is 266 nm, the depth of focus is ±0.16 $\mu$m. The focal point position of this short depth of focus is extremely difficult to adjust by a manual operation each time the inspection is to be performed. So, in the microscopic device for semiconductor inspection employing a UV light source, there is required a mechanism for making an auto-focussing accurately and speedily without relying upon a manual operation.

SUMMARY OF THE INVENTION

It is therefore an object of the present invention to provide a mechanism and a method for controlling the focal point position of the UV light in which auto-focussing of the converged UV light can be realized accurately and speedily, and a method and apparatus for inspecting a device employing the converged UV light in which auto-focussing the converged UV light can be realized accurately and speedily.

In one aspect, the present invention provides a focal point position control mechanism for UV light including supporting means for supporting an object of illumination, UV light illuminating means for illuminating UV light, converged by an objective lens, onto the object of illumination carried by the supporting means, distance detection means mounted at a fixed position with respect to the objective lens for detecting the distance to the object of illumination, and position control means for shifting the supporting means and/or the objective lens for controlling the relative position between the object of illumination and the objective lens. The position control means controls the distance between the object of illumination and the objective lens to a pre-set target distance based on the distance detected by the distance detection means.

With the present focal point position control mechanism, the objective lens and the object of illumination are moved relatively to each other, based on the distance as detected by distance detection means, the distance therebetween is used as a pre-set target distance, and the focal point position of the UV light converged by the objective lens is brought into coincidence with an optional position of the object of illumination.

In the focal point position control method for UV light according to the present invention, the distance to the object of illumination is detected by a distance detection device mounted at a fixed position relative to the objective lens. The distance between the object of illumination and the objective lens is controlled to a pre-set target distance based on the distance as detected by the distance detection device.

In the present focal point position control method for UV light, the objective lens and the object of illumination is moved relative to each other so that the distance therebetween will be a pre-set target distance. The focal point position of the UV light converged by the objective lens is brought into coincidence with an optional position of the object of illumination.

In another aspect, the present invention provides a inspection apparatus including supporting means for supporting a device, UV light illuminating means for illuminating UV light, converged by an objective lens, onto the device carried by the supporting means, distance detection means mounted at a fixed position with respect to the objective lens for detecting the distance to the device, position control means for shifting the supporting means and/or the objective lens for controlling the relative position between the device and the objective lens, UV light photographing means for detecting the reflected UV light illuminated on the device for photographing an image of the device, and inspection means for processing the image as photographed by the UV light photographing means for inspecting the device. The position control means controls the distance between the device and the objective lens to a pre-set target distance based on the distance detected by the distance detection means.

In this inspection apparatus, the objective lens and the object of illumination are moved relatively to each other so that the distance therebetween will be a pre-set target distance and so that the focal point position of the UV light converged by the objective lens will be coincident with an optional position of the object of illumination. With the present inspection apparatus, the reflected light of the UV light illuminated on the device is detected to photograph and inspect the device image.

In yet another aspect, the present invention provides an inspection method in which the UV light converged by an objective lens is illuminated on a device to detect the reflected light to inspect the device, in which the method includes detecting the distance to the device by a distance detection device mounted at a fixed position relative to the objective lens, controlling the distance between the device and the objective lens to a pre-set target distance based on the distance as detected by the distance detection device, illuminating the UV light converged by the objective lens, detecting the reflected light of the UV light illuminated on the device to photograph an image of the device and processing the image of the device as photographed for inspecting the device.

In the present inspection method, the objective lens and the object of illumination are moved relatively to each other and the distance therebetween is used as a pre-set target distance. The focal point position of the UV light, converged by the objective lens, is brought into coincidence with an optional position of the object of illumination. In this inspection method, the reflected light of the UV light illuminated on the device is detected to photograph an image of the device for inspection.

In the focal point position control mechanism and method for UV light, according to the present invention, the objective lens and the object of illumination are relatively moved, based on a distance as measured by the distance detection means or apparatus, and the distance therebetween is used as a pre-set target distance. The focal point position of the UV light converged by the objective lens is brought into coincidence with an optional position of the object of illumination.

With the focal point position control mechanism and method according to the present invention, the UV light converged by the objective lens can be auto-focussed accurately, speedily and extremely readily.

In the inspection method and apparatus according to the present invention, the objective lens and the object of illumination are relatively moved, based on a distance detected by the distance detection means and device, so that the distance therebetween will be a pre-set target distance. The focal point position of the UV light converged by the objective lens is brought into coincidence with an optional position of an object of illumination. With the present inspection method and device, the reflected light o the UV light illuminated on the device is detected to photograph and inspect he device image.

So, in the present inspection method and device, the UV light, converged by the objective lens, can be auto-focussed accurately, speedily and extremely readily to permit inspection of fine defects on a device.

BRIEF DESCRIPTION OF THE DRAWINGS

FIG. 16 illustrates a matrix table for storage of a first correction value.

DESCRIPTION OF THE PREFERRED EMBODIMENTS

Figure 1:
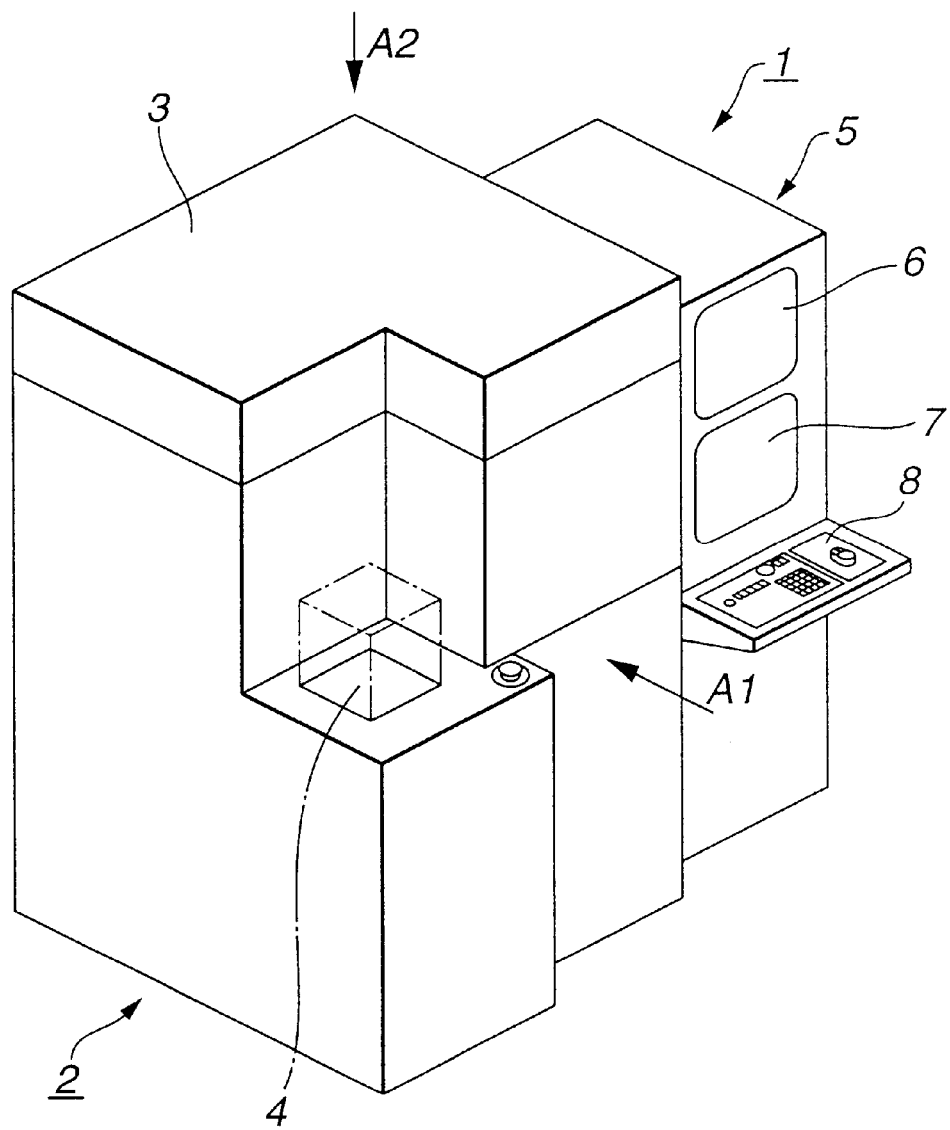
FIG. 1 shows the appearance of an inspection device according to the present invention.

Referring to the drawings, preferred embodiments of according to the present invention will be explained in detail.

FIG. 1 shows the appearance of an inspection device according to the present invention. This inspection device 1 is designed to inspect a semiconductor wafer carrying a pre-set device pattern. If a defect is found in a semiconductor wafer carrying a pre-set device pattern, the inspection device scrutinizes into the nature of the defect to proceed to classification.

Referring to FIG. 1, this inspection device 1 has a dust-proofing function, and includes a clean unit 2 for keeping the inner environment clean. The clean unit 2 has, on its upper portion, a clean air unit 3 for furnishing clean air freed of contaminants. From this clean air unit 3, clean air freed of contaminants is furnished to keep the cleanness of the inner environment approximately at a class 1 cleanness.

This inspection device 1 inspects the semiconductor wafer, having the pre-set device pattern formed thereon, in the clean unit 2. The semiconductor wafer, as an article to be inspected, is transported as it is hermetically sealed in a pre-set hermetically sealed vessel 4, so as to be transferred through the vessel 4 into the clean unit 2. That is, when inspecting a semiconductor wafer, the vessel 4 charged with the semiconductor wafer is mounted on the clean unit 2, as indicated by a chain line in FIG. 1. The semiconductor wafer is taken out from the vessel 4, by a transporting robot, as later explained, to keep the wafer in a state unexposed to ambient air, and is mounted on an inspection stage provided within the clean unit 2.

By inspecting the semiconductor wafer within the clean unit 2, it is possible to prevent contaminants from becoming affixed to the semiconductor wafer during inspection. Moreover, if the semiconductor wafer to be inspected is transported as it is kept in the hermetically sealed vessel 4, and is transferred through this vessel 4 into the clean unit 2, it is possible to prevent contaminants from becoming affixed to the semiconductor wafer, by keeping only the insides of the clean unit 2 and the vessel 4 to sufficient cleanliness, without it being necessary to elevate the degree of cleanliness of the entire environment in which the inspection device 1 is installed.

By locally elevating the degree of cleanliness only of the required site, the high degree of cleanliness may be maintained, whilst the cost for realizing a clean environment can be suppressed appreciably. As a mechanical interface between the hermetically sealed vessel 4 and the clean unit 2, a so-called standard mechanical interface (SMI) is preferred. In such case, the so-called SMIF-POD is used as the hermetically sealed vessel 4. Exteriorly of the clean unit 2, the inspection device 1 includes an external unit 5 provided with e.g., a computer for operating the inspection device 1. This external unit 5 is provided with a display device 6 for demonstrating e.g., a photographed image of a semiconductor wafer, a display unit 7 for demonstrating the various inspection conditions, and with an input device 8 for inputting a command to the inspection device 1. An operator in charge of inspection of a semiconductor wafer inputs necessary commands from the input device 8 arranged in the external unit 5 to execute the semiconductor wafer inspection, as he views the display devices 6, 7 arranged on the external unit 5.

Figure 2:
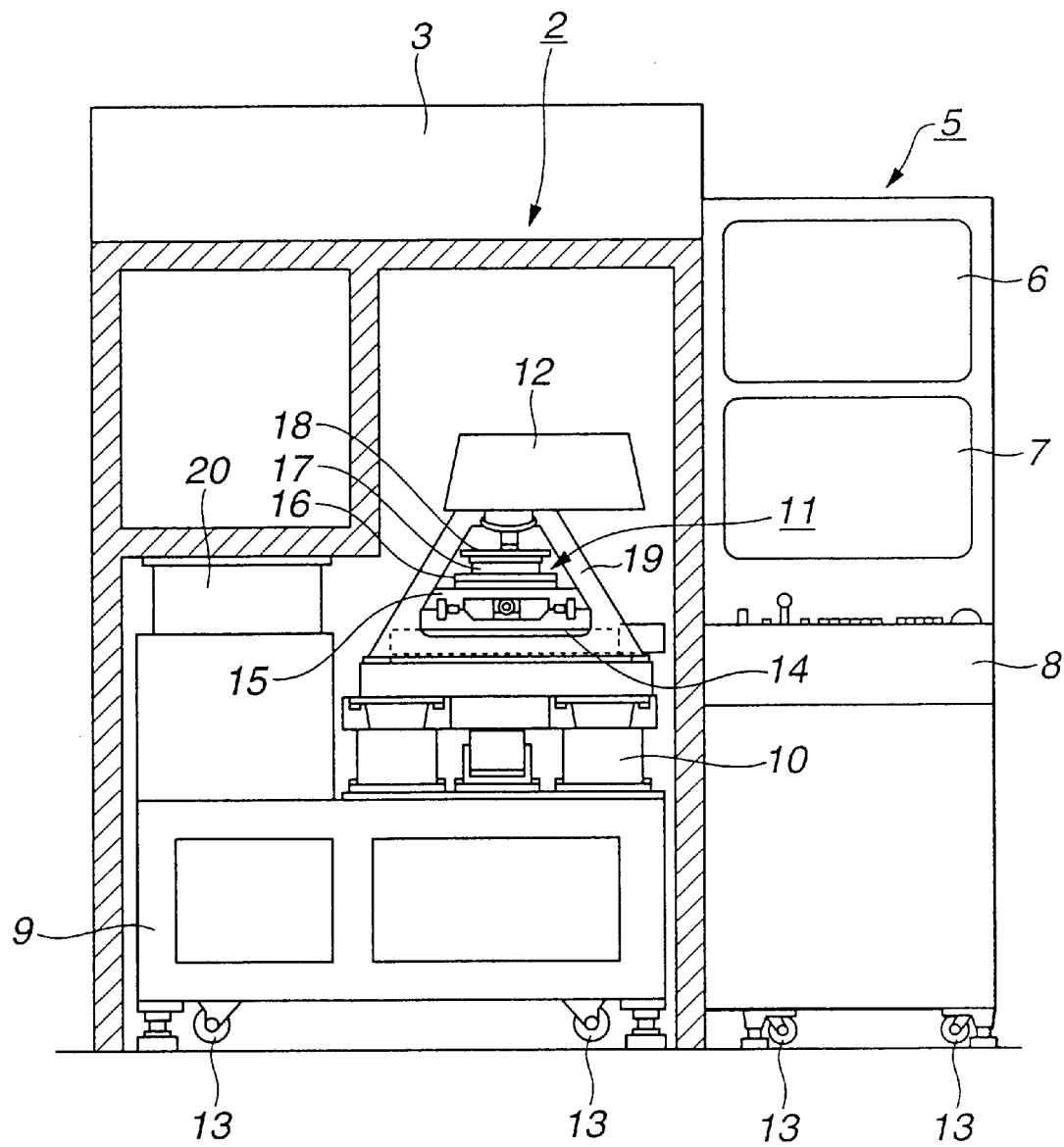
FIG. 2 is a front view showing an internal structure of a clean unit of the inspection device shown in FIG. 1, and looking into the inside of the clean unit in the direction indicated by arrow A1 in FIG. 1.
Figure 3:
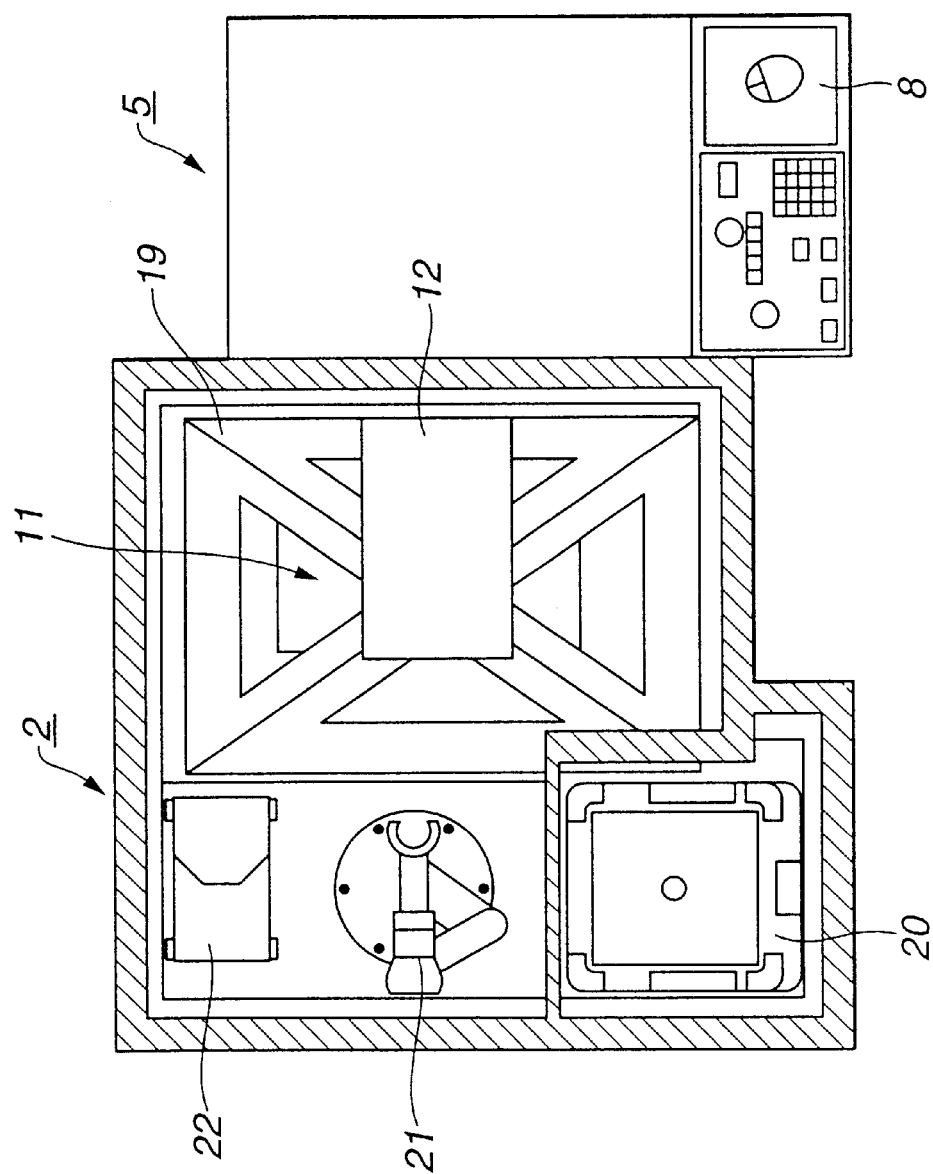
FIG. 3 is a plan view showing an internal structure of a clean unit of the inspection device shown in FIG. 1, and looking into the inside of the clean unit in the direction indicated by arrow A2 in FIG. 1.

Referring to FIGS. 2 and 3, the interior of the clean unit 2 of the inspection device 1 is explained. FIG. 2 is a front view showing the interior of the clean unit 2 looking in the direction indicated by arrow A1 in FIG. 1, whereas FIG. 3 is a plan view showing the interior of the clean unit 2 looking in the direction indicated by arrow A2 in FIG. 1.

Referring to FIG. 2, there are mounted, in the clean unit 2, a support base 9, an anti-vibration base 10, an inspection stage 11, mounted on the anti-vibration base 10, and an optical unit 12, mounted on the anti-vibration base 10.

The support base 9 is used for supporting the components arranged in the clean unit 2. On the bottom parts of the support base 9 and the external unit 5 are mounted tires 13 by means of which the inspection device 1 can be moved easily. Meanwhile, in securing the inspection device 1, securing legs are set on the floor to keep the tires 13 floated, as shown in FIG. 2.

The anti-vibration base 10 suppresses oscillations emanating from the floor or those produced when shifting the inspection stage 11. Since it is the semiconductor wafer carrying a fine device pattern that is to be inspected by this inspection device 1, the slightest oscillations prove hindrance to the inspecting operations. So, this inspection device 1 uses the anti-vibration base 10 to suppress the oscillations.

As the anti-vibration base, used in this inspection device 1, a so-called active anti-vibration base is preferred. The anti-vibration base 10 detects the oscillations to operate in the direction of cancelling the oscillations to remove the oscillations quickly, and is superior in oscillation-proofing effect.

In this inspection device 1, which performs the inspection at a high resolution, using the UV light, the effect of the oscillations tend to present itself significantly. However, by employing the anti-vibration base, superior in the anti-oscillation effect, as the anti-vibration base 10 for the inspection device 1, it is possible to suppress the effect of the oscillations to improve the inspection performance in the high-resolution inspection employing the UV light.

On the anti-vibration base 10 is mounted the inspection stage 11 which is a stage for supporting the semiconductor wafer as an article being inspected. This inspection stage 11 has the function not only of supporting the semiconductor wafer as an article being inspected, but also of shifting the semiconductor wafer to a pre-set inspecting position.

Specifically, the inspection stage 11 includes an X-stage 14, mounted on the anti-vibration base 10, an Y-stage 15, set on the X-stage 14, a θ-stage 16, set on the Y-stage 15, a Z-stage 17, set on the θ-stage 16, and a suction plate 18, mounted on the Z-stage 17.

The X-stage 14 and the Y-stage 15 are stages moved in the horizontal direction. Specifically, the X-stage 14 and the Y-stage 15 are configured for being moved in mutually orthogonal directions. During semiconductor wafer inspection, the semiconductor wafer is moved to a position of inspection by the X-stage 14 and the Y-stage 15.

The θ-stage 16 is a so-called rotating stage and is adapted for rotating the semiconductor wafer. During semiconductor wafer inspection, the semiconductor wafer is rotated by the θ-stage 16 so that a device pattern on the semiconductor wafer will be horizontal or vertical, for example, with respect to the screen.

The Z-stage 17 is movable in the perpendicular direction for adjusting the stage height. During semiconductor wafer inspection, the stage height is adjusted by the Z-stage 17 so that the inspection surface of the semiconductor wafer will be of an appropriate height.

The suction plate 18 is used for securing the semiconductor wafer being inspected under suction. During semiconductor wafer inspection, the semiconductor wafer being inspected is set on this suction plate 18. The semiconductor wafer is sucked against movement by the suction plate 18.

On the anti-vibration base 10 is arranged the optical unit 12 which is supported by a supporting member 19 so as to lie on the inspection stage 11. During semiconductor wafer inspection, this optical unit 12 serves for photographing an image of the semiconductor wafer. This optical unit 12 has both the function of photographing the image of the semiconductor wafer being inspected with a low resolution using the visible light and the function of photographing the image of the semiconductor wafer being inspected with a high resolution using the UV light.

Within the clean unit 2 is arranged an elevator 20 set on the support base 9, as shown in FIGS. 2 and 3. Within the clean unit 2, there are also arranged a transporting robot 21 as set on the support base 9 and an aligner 22 as set on the support base 9.

The elevator 20, transporting robot 21 and the aligner 22 serve for taking out semiconductor wafers transported as they are charged in the hermetically sealed vessel 4, such as SMIF-POD, out of the vessel 4 for setting the semiconductor wafers on the inspection stage 11.

In inspecting the semiconductor wafer, the semiconductor wafer first is charged into the hermetically sealed vessel 4 and transported. The vessel 4 is then mounted on the clean unit 2 as indicated by a chain line in FIG. 1. The semiconductor wafer is taken out by the elevator 20 from the bottom of the vessel 4 to preclude intrusion of outside air into the interior of the clean unit 2. The semiconductor wafer is housed in a magazine and is charged along with the magazine in the hermetically sealed vessel 4. From the elevator 20, the semiconductor wafers are taken out along with the magazine and lowered.

From among the semiconductor wafers, lowered by the elevator 20 along with the magazines and taken out from the vessel, the semiconductor wafer to be inspected is selected and taken out along with the magazine from the vessel 4 by the transporting robot 21. The distal end of the transporting robot 21 is fitted with a suction mechanism for sucking and enabling the transport of the semiconductor wafer.

The semiconductor wafer, taken out from the magazine by the transporting robot 21, is transported to the aligner 22. The aligner 22 effects phasing and centering of the semiconductor wafer, with an orientation flat and a notch, previously provided to the semiconductor wafer, as reference. The semiconductor wafer, thus phased and centered, is again sucked by the transporting robot 21 and transported to the inspection stage 11 where it is mounted on the suction plate 18.

As an example of a mechanism for taking out the semiconductor wafer, transported as it is charged in the hermetically sealed vessel 4, and for mounting it on the inspection stage 11, such a one comprising the elevator 20, transporting robot 21 and the aligner 22 is shown above. However, as a matter of course, the mechanism for taking out the semiconductor wafer from the vessel 4 for placing it on the inspection stage 11 is not limited to the above-given example, that is, any other suitable mechanism than that given above may be used, provided that, by such mechanism, the semiconductor wafer transported as it is charged in the hermetically sealed vessel 4 can be taken out from the vessel and set on the inspection stage 11 without being exposed to ambient atmosphere.

Figure 4:
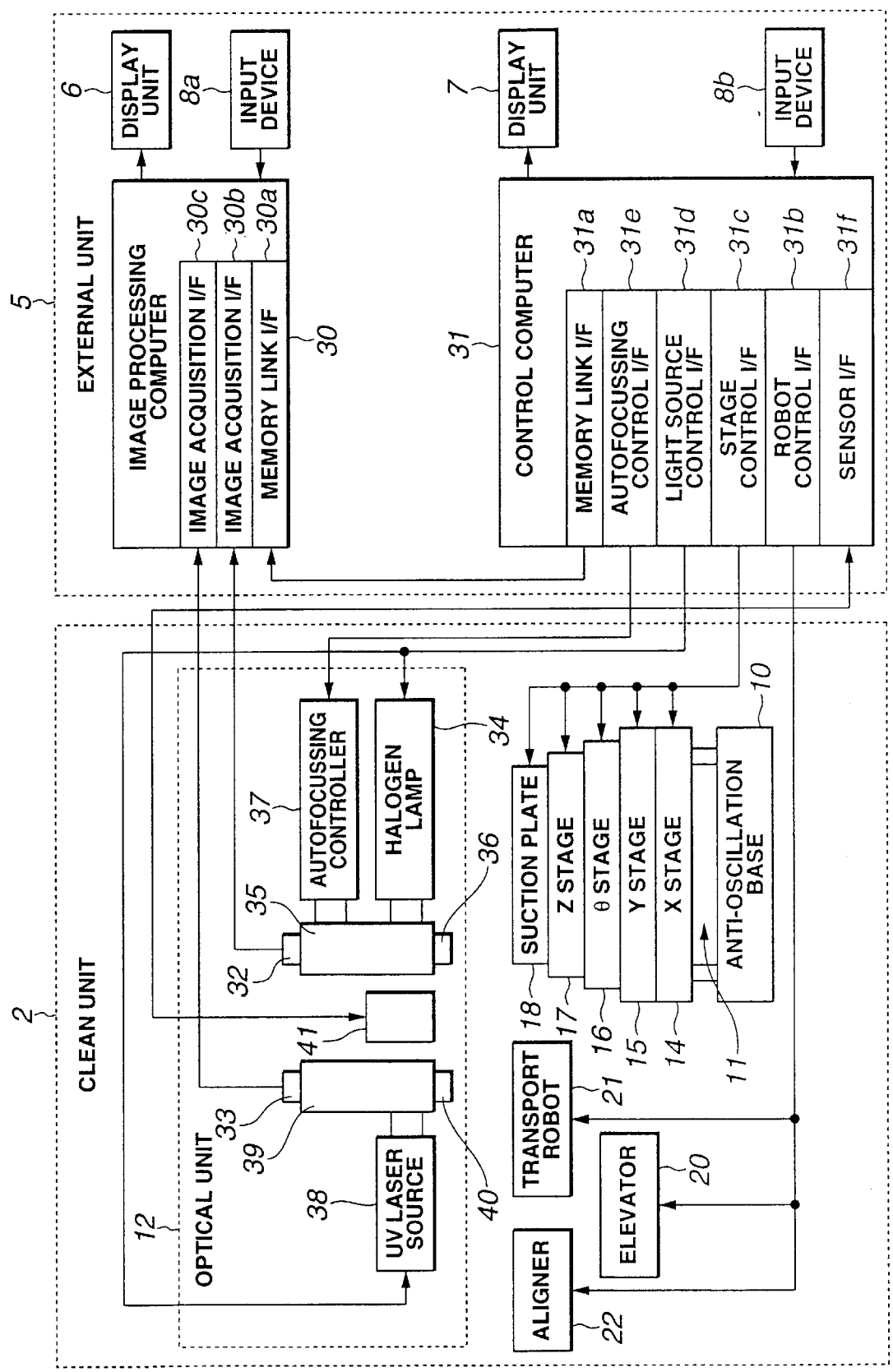
FIG. 4 is a block diagram showing the structure of the inspection device shown in FIG. 1.

Referring to the block diagram of FIG. 4, the above-described inspection device 1 is explained more specifically.

Referring to FIG. 4, an image-processing computer 30, to which are connected the display device 6 and an input device 8a, and a control computer 31, to which are connected the display device 7 and an input device 8b, are arranged on the external unit 5 of the inspection device 1. It is noted that, in FIGS. 1 and 2, the input device 8b, connected to the image-processing computer 30, and the input device 8b, connected to the control computer 31, are collectively termed the input device 8.

The image-processing computer 30 is such a computer which, in inspecting the semiconductor wafer, captures a photographed image of the semiconductor wafer by CCD (charge-coupled device) cameras arranged within the optical unit 12. That is, the present inspection device 1 inspects the semiconductor wafer by analyzing the image of the semiconductor wafer photographed by the CCD cameras 32, 33 installed in the optical unit 12 by processing with the image-processing computer 30.

Meanwhile, the input device 8a, connected to the image-processing computer 30, inputs commands required for analyzing an image acquired from the CCD cameras 32, 33, to the image-processing computer 30, and are made up e.g., of a pointing device, such as a mouse, or a keyboard. The display device 6, connected to the image-processing computer 30, demonstrates e.g., the results of analysis of the image acquired from the CCD cameras 32, 33, and is made up e.g., of a CRT display, a liquid crystal display and so forth.

The control computer 31 is used for controlling the inspection stage 11, elevator 20, transporting robot 21, aligner 22 and respective equipment in the inside of the optical unit 12, in inspecting the semiconductor wafer. Specifically, this inspection device 1 controls the inspection stage 11, elevator 20, transporting robot 21, aligner 22 and respective equipment in the inside of the optical unit 12, in inspecting the semiconductor wafer, so that the image of the semiconductor wafer being inspected will be photographed by the CCD cameras 32, 33 installed in the interior of the optical unit 12.

Meanwhile, the input device 8b, connected to the control computer 31, serves for inputting commands necessary for controlling the inspection stage 11, elevator 20, transporting robot 21, aligner 22 and respective equipment in the inside of the optical unit 12, to the control computer 31, and is made up of a pointing device, such as a mouse, or a keyboard. The display device 7, connected to the control computer 31, demonstrates e.g., a variety of conditions in inspecting the semiconductor wafer, and is made up e.g., of a CRT display, a liquid crystal display and so forth.

The image-processing computer 30 and the control computer 31 are able to exchange data reciprocally by a memory linking mechanism. Specifically, the image-processing computer 30 and the control computer 31 are interconnected by respective memory linking interfaces 30a, 31a, to enable the reciprocal data exchange between the image-processing computer 30 and the control computer 31.

Within the interior of the clean unit 2 of the inspection device 1, the elevator 20, transporting robot 21 and the aligner 22 are arranged, as described above, as a mechanism for taking out the semiconductor wafer, charged into the hermetically sealed vessel 4 and transported in this state, from the vessel, 4 to set the semiconductor wafer thus taken out on the inspection stage 11. These devices are connected to the control computer 31 through a robot control interface 31*b*. The elevator 20, transporting robot 21 and the aligner 22 are fed with a control signal from the control computer 31 through the robot control interface 31*b*.

That is, in taking out the semiconductor wafer, charged into the hermetically sealed vessel 4 and transported in this state, from the vessel 4, and in setting the semiconductor wafer thus taken out on the inspection stage 11, the control signal is sent from the control computer 31 through the robot control interface 31*b* to the elevator 20, transporting robot 21 and the aligner 22. Based on this control signal, the elevator 20, transporting robot 21 and the aligner 22 take out the semiconductor wafer, transported in the hermetically sealed vessel 4, from the vessel 4, to et the semiconductor wafer on the inspection stage 11.

Within the interior of the clean unit 2 of the inspection device 1 is arranged the anti-vibration base 10, on which are installed the inspection stage 11 including the X-stage 14, Y-stage 15, θ-stage 16, Z-stage 17 and the suction plate 18.

It is noted that the X-stage 14, Y-stage 15, θ-stage 16, Z-stage 17 and the suction plate 18 are connected through a stage control interface 31*c* to the control computer 31 provided in the external unit 5. The X-stage 14, Y-stage 15, θ-stage 16, Z-stage 17 and the suction plate 18 are fed with control signals from the control computer 31 through the stage control interface 31*c*.

In inspecting the semiconductor wafer, control signals are issued from the control computer 31 through the stage control interface 31*c* to the X-stage 14, Y-stage 15, θ-stage 16, Z-stage 17 and the suction plate 18. Based on the control signals, the X-stage 14, Y-stage 15, θ-stage 16, Z-stage 17 and the suction plate 18 are actuated to suck and secure the semiconductor wafer being inspected by the suction plate 18, whilst the X-stage 14, Y-stage 15, θ-stage 16 and the Z-stage 17 are actuated so that the semiconductor wafer will be of a pre-set position, a pre-set angle and a pre-set height.

On the anti-vibration base 10 is mounted the optical unit 12 which serves for imaging the semiconductor wafer in inspecting the semiconductor wafer and which has both the function of photographing the image of the semiconductor wafer being inspected to low resolution using the visible light and the function of photographing the image of the semiconductor wafer being inspected to high resolution using the UV light, as described above.

Within this optical unit 12 are arranged, as a mechanism for photographing an image of the semiconductor wafer with visible light, a CCD camera for visible light 32, a halogen lamp 34, an optical system for visible light 35, an objective lens for visible light 36 and an auto-focussing unit for visible light 37.

In photographing the image of the semiconductor wafer with the visible light, the halogen lamp 34 is turned on. It is noted that the halogen lamp 34 has its driving source connected through a light source control interface 31*d* to the control computer 31 arranged in the external unit 5. The driving source of the halogen lamp 34 is fed with a control signal through a light source control interface 31*d* from the control computer 31. The halogen lamp 34 is turned on and off based on this control signal.

For photographing the image of the semiconductor wafer with the visible light, the halogen lamp 34 is turned on so that the visible light therefrom is illuminated on the semiconductor wafer through the optical system for visible light 35 and the objective lens for visible light 36 on the semiconductor wafer to illuminate the latter. The image of the semiconductor wafer, thus illuminated by the visible light, is enlarged by the objective lens for visible light 36, with the enlarged image being then photographed by the CCD camera for visible light 32.

It is noted that the CCD camera for visible light 32 is connected through an image retrieving interface 30*b* to the image-processing computer 30 arranged in the external unit 5. The image of the semiconductor wafer, photographed by the CCD camera for visible light 32, is retrieved by the image-processing computer 30 through the image retrieving interface 30*b*.

In photographing the image of the semiconductor wafer with the visible light, as described above, an auto-focussing operation is carried out under control by the auto-focussing unit for visible light 37. Specifically, the auto-focussing unit for visible light 37 detects whether or not the separation between the objective lens for visible light 36 and the semiconductor wafer coincides with the focal length of the objective lens for visible light 36. In case of non-coincidence, the objective lens for visible light 36 or the Z-stage 17 is moved to bring the plane of inspection of the semiconductor wafer into coincidence with the focal plane of the objective lens for visible light 36.

It is noted that the auto-focussing unit for visible light 37 is connected to the control computer 31 arranged in the external unit 5 through an auto-focussing control interface 31*e*. The auto-focussing unit for visible light 37 is fed with a control signal from the control computer 31 through the auto-focussing control interface 31*e*. The auto-focussing of the objective lens for visible light 36 under control by the auto-focussing unit for visible light 37 takes place based on this control signal.

Within the interior of the optical unit 12 are arranged a CCD camera for UV light 33, a laser light source for UV light 38, an optical system for UV light 33, an objective lens for UV light 40 and a distance sensor 41, as a mechanism for photographing the image of the semiconductor wafer with the UV light.

In photographing an image of the semiconductor wafer with the UV light, the laser light source for UV light 38 is turned on. It is noted that the driving source of the laser light source for UV light 38 is connected through the light source control interface 31*d* to the control computer 31 arranged in the external unit 5. The driving source of the laser light source for UV light 38 is fed with the control signal from the control computer 31 through the light source control interface 31*d*. The laser light source for UV light 38 is turned on/off based on this control signal.

Meanwhile, the upper limit wavelength of the UV solid laser, usable for practical industrial application, is 355 nm. Desirably, such a light source radiating the UV laser light with the wavelength not longer than 355 nm is used as the laser light source for UV light 38. The UV laser light with the wavelength of 355 nm is obtained as a tripled wave of the YAG laser. It is also possible to obtain the UV laser light with the wavelength of 266 nm as a quadrupled wave of the YAG laser. As a laser light source, such a one with an oscillation wavelength of 166 nm has also been developed. This laser light source may also be used as the laser light source for UV light 38. It is noted that, for improving the resolution, the UV laser light, radiated from the laser light source for UV light 38, is desirably of a shorter wavelength. However, if the wavelength is too short, it is difficult to realize an optical system matched to the wavelength. Therefore, the wavelength λ of the UV laser radiated from the laser light source for UV light 38 is desirably of the order of 355 to 166 nm.

In photographing an image of the semiconductor wafer with the UV light, the laser light source for UV light 38 is turned on, and the UV light from the laser light source for UV light 38 is illuminated on the semiconductor wafer through the optical system for UV light 39 and the objective lens for UV light 40 to illuminate the semiconductor wafer. The image of the semiconductor wafer, illuminated by the UV light, is enlarged by the objective lens for UV light 40, and the resulting enlarged image is photographed by the CCD camera for UV light 33.

It is noted that the CCD camera for UV light 33 is connected through an image retrieving interface 30c to the image-processing computer 30 arranged in the external unit 5. The image of the semiconductor wafer, photographed by the CCD camera for UV light 33, is retrieved through the image retrieving interface 30 c by the image-processing computer 30.

In photographing the image of the semiconductor wafer by the UV light as described above, auto-focussing of the objective lens for UV light 40 is carried out using the distance sensor 41. That is, the separation between the objective lens for UV light 40 and the semiconductor wafer is detected by the distance sensor 41, and the objective lens for UV light 40 or the Z-stage 17 is moved, based on the result of detection, so that the plane of inspection of the semiconductor wafer is brought into coincidence with the focal plane of the objective lens for UV light 40.

The distance sensor 41 is connected through a sensor interface 31f to the control computer 31 provided in the external unit 5. The distance sensor 41 is fed with a control signal from the control computer 31 through the sensor interface 31f. The distance sensor 41 is responsive to this control signal to detect the distance to the semiconductor wafer to send the detected result through the sensor interface 31f to the control computer 31. Based on the distance detected by the distance sensor 4 1, the control computer 31 causes movement of the X-stage 14, Y-stage 15 and the Z-stage 17 to effect auto-focussing o the objective lens for UV light 40.

As this distance sensor 41, a capacitance type sensor, for example, is used. The capacitance type sensor measures the capacitance between it and an article being measured to make contact-free measurement of the distance between the sensor and the article being measured. When the capacitance type sensor is used as the distance sensor 41, the full measurement scale is e.g., ±10V/±100 μm.

Figure 5:
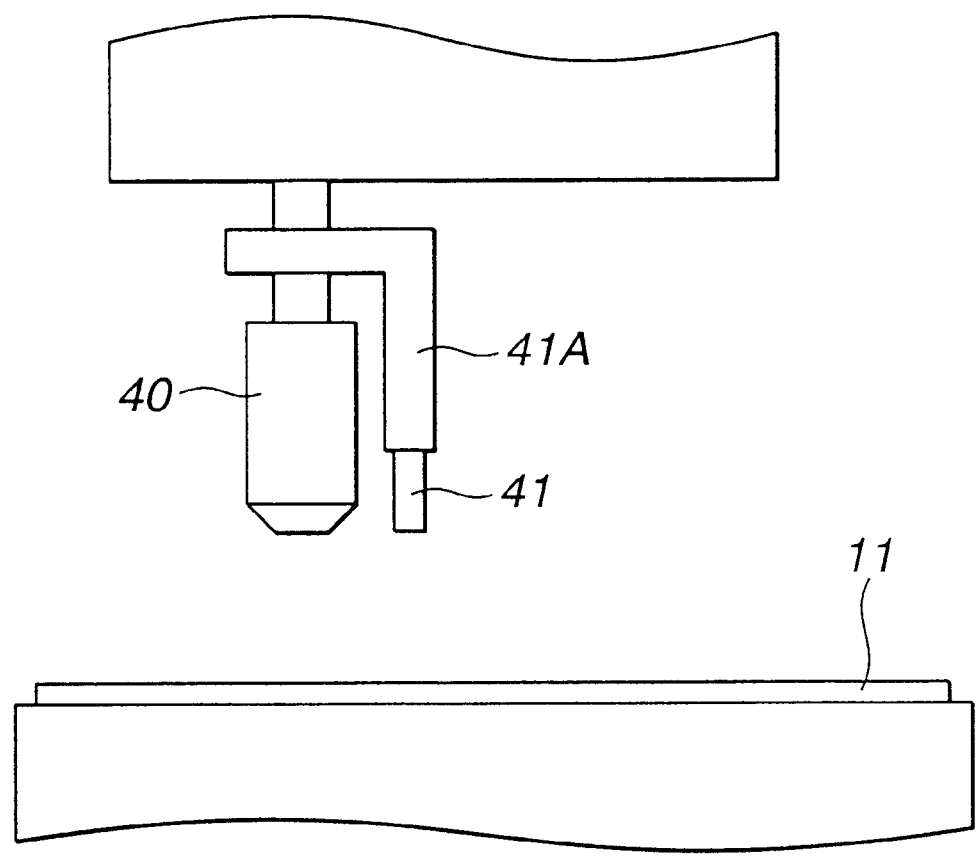
FIG. 5 shows an illustrative structure of a distance sensor and an objective lens for UV light.

The distance sensor 41 is mounted within the optical unit 12 at a fixed relative position with respect to the objective lens for UV light 40. For example, the distance sensor 41 is secured to the objective lens for UV light 40 through a connecting member 41a at a substantially equal height level (perpendicular position) to that of the objective lens for UV light 40, as shown in FIG. 5. This distance sensor 41 detects the distance in the light radiating direction of the UV light illuminated on the semiconductor wafer through the objective lens for UV light 40. That is, the distance sensor 41 detects the distance in the perpendicular direction between the distance sensor 41 and the semiconductor wafer.

The optical system of the optical unit 12 of the inspection device 1 is explained in further detail with reference to FIG. 6. Meanwhile, the explanation on the auto-focussing controllers 37, 41 is omitted and the explanation is made of the optical system illuminating the semiconductor wafer being inspected and the optical system for imaging the semiconductor wafer being inspected.

Figure 6:
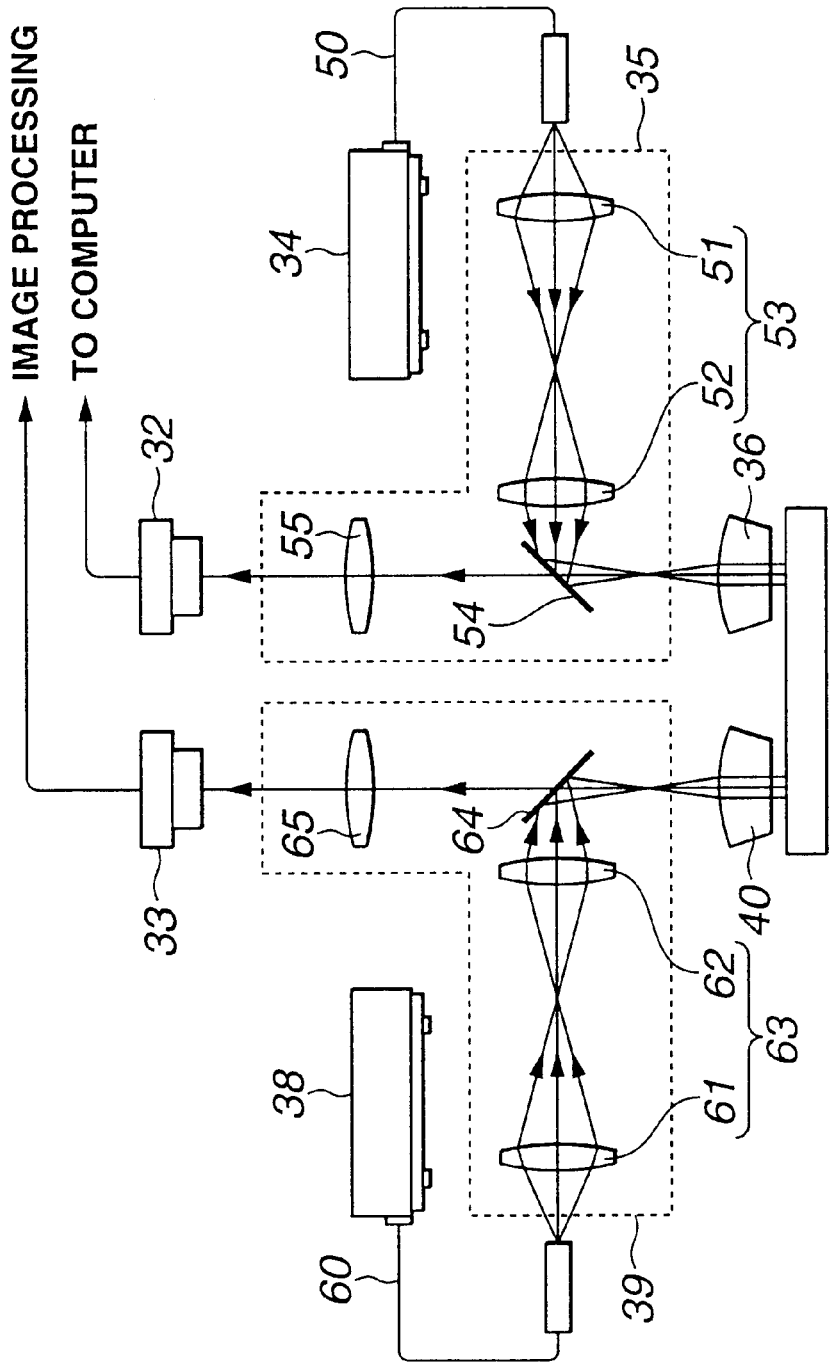
FIG. 6 shows an illustrative structure of an optical system of an optical unit of the inspection device shown in FIG. 1.

Referring to FIG. 6, the optical unit 12 includes, as an optical system for photographing an image of the semiconductor wafer by the visible light, the halogen lamp 34, optical system for visible light 35 and the objective lens for visible light 36.

The visible light from the halogen lamp 34 is forwarded by an optical fiber 50 to the optical system for visible light 35. It is noted that the optical system for visible light 35 includes an illuminating optical system 53, made up of lenses 51, 52, with the visible light forwarded by the optical fiber 50 to the optical system for visible light 35 first falling on the illuminating optical system 53. The visible light, forwarded by the optical fiber to the optical system for visible light 35, falls on the half mirror 54 and is reflected thereby towards the objective lens for visible light 36 so as to fall on the semiconductor wafer through the objective lens for visible light 36. This illuminates the semiconductor wafer with the visible light.

The image of the semiconductor wafer, illuminated by the visible light, is enlarged by the objective lens for visible light 36 and photographed by the CCD camera for visible light 32. That is, the reflected light from the semiconductor wafer, illuminated by the visible light, falls on the CCD camera for visible light 32 through the objective lens for visible light 36, a half mirror 54 and an imaging lens 55, whereby an enlarged image of the semiconductor wafer is photographed by the CCD camera for visible light 32. The image of the semiconductor wafer, photographed by the CCD camera for visible light 32, referred to below as the visible image, is sent to the image-processing computer 30.

The optical unit 12 includes, as an optical system for photographing an image of the semiconductor wafer with UV light, the laser light source for UV light 38, optical system for UV light 39 and the objective lens for UV light 40.

The UV light from the laser light source for UV light 38 is forwarded by an optical fiber 60 to the optical system for UV light 39. The optical system for UV light 39 includes an optical system for illumination 63, constructed by the two lenses 61, 62. The UV light, forwarded by the optical fiber 60 to the optical system for UV light 39, first falls on the optical system for illumination 63. The UV light, forwarded by the optical fiber 60 to the optical system for UV light 39, is incident on a half mirror 64 through the optical system for illumination 63 and thereby reflected by the half mirror 64 towards the objective lens for UV light 40 to fall therethrough on the semiconductor wafer to illuminate the latter with the UV light.

The image of the semiconductor wafer, illuminated by the UV light, is enlarged by the objective lens for UV light 40 and photographed by the CCD camera for UV light 33. That is, the reflected light from the semiconductor wafer, illuminated by the UV light, falls on the CCD camera for UV light 33 through the objective lens for UV light 40, half mirror 64 and an imaging lens 65, whereby the enlarged image of the semiconductor wafer is photographed by the CCD camera for UV light 33. The image of the semiconductor wafer, as photographed by the CCD camera for UV light 33 (referred to below as UV image), is sent to the image-processing computer 30.

Figure 7:
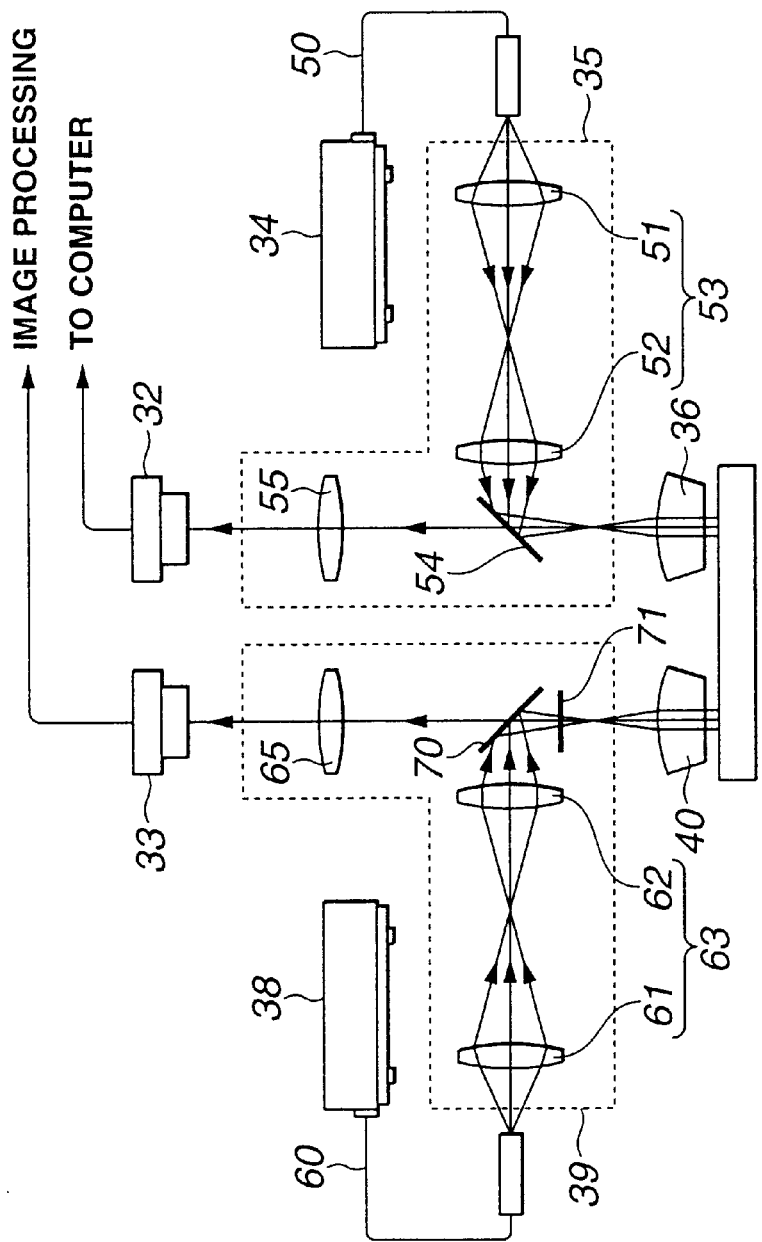
FIG. 7 shows another illustrative structure of an optical system of an optical unit of the inspection device shown in FIG. 1.

In the optical system for UV light 39, a polarizing beam splitter 70 may be provided in place of the half mirror 64, and a quarter wave plate 71 may be provided between the polarizing beam splitter 70 and the objective lens for UV light 40, as shown in FIG. 7. By employing this structure, the UV laser can be utilized efficiently.

In the above-described inspection device 1, in which the image of the semiconductor wafer can be photographed and inspected by the UV light which is the light of a shorter wavelength than the visible light, it is possible to detect or classify finer defects than if the visible light is used to perform defect detection or classification.

Moreover, in the inspection device 1, provided with both the optical system for visible light and that for UV light, it is possible to effect the semiconductor wafer inspection with a low resolution using the visible light and that with a high resolution using the UV light. Therefore, with the inspection device 1, it is possible to detect or classify coarser defects by the semiconductor wafer inspection at lower resolution employing the visible light as well as to detect or classify finer defects by the semiconductor wafer inspection at higher resolution employing the UV light.

Meanwhile, in the above-described inspection device 1, a larger numerical aperture NA of the objective lens for UV light 40 is desirable. For example, it is set to 0.9 or higher. By employing a lens with a higher numerical aperture NA as the objective lens for UV light 40, it is possible to detect finer defects.

Meanwhile, if the semiconductor wafer defect is made up only of crests and recesses, such as grazing, and is devoid of the color information, such defect is hardly perceptible with the incoherent light. If conversely the light with high coherency, such as laser light, even the defect made up only of crests and recesses, and devoid of the color information, can be viewed clearly because the light undergoes interference in the vicinity of a step difference of the crests and recesses. The inspection device 1 uses the laser light source for UV light 38, radiating the laser light of the ultraviolet range, as the UV light source. Therefore, in the inspection device 1, the defect made up only of crests and recesses and which is devoid of the color information, such as grazing, can be detected clearly. That is, with the above-described inspection device 1, the phase information, difficult to locate with the visible light (incoherent light) from the halogen lamp 34, can be detected easily using the UV laser light (coherent light) from the laser light source for UV light 38.

Figure 8:
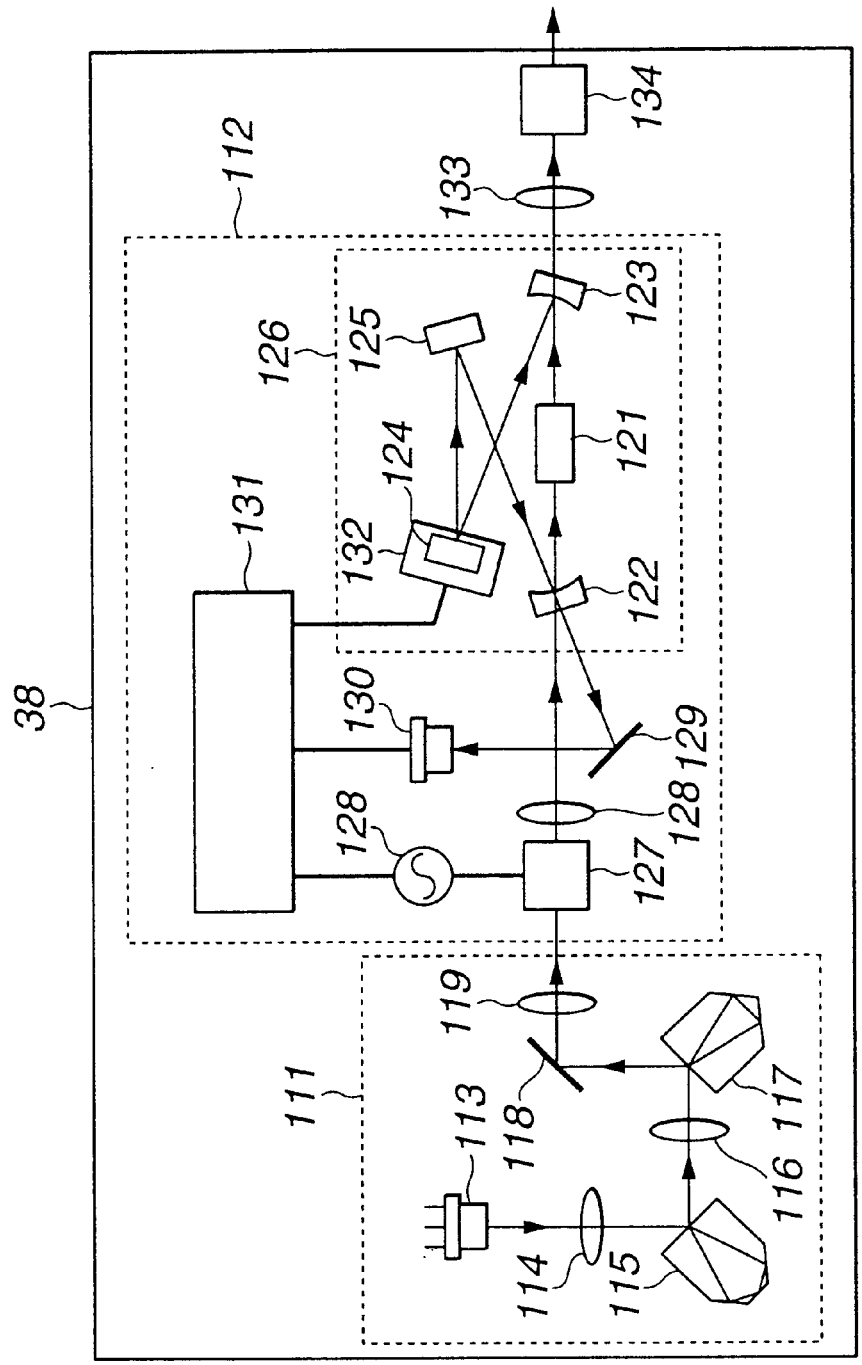
FIG. 8 shows another illustrative structure of a UV laser light source of the inspection device shown in FIG. 1.

An illustrative structure of the laser light source for UV light 38, used in the inspection device 1, is explained in further detail by referring to FIG. 8.

The laser light source for UV light 38, shown in FIG. 8, transforms the wavelength of the laser light from the solid laser light source to generate and emit the UV laser light. This laser light source for UV light 38 includes a green laser light generating unit 111 for generating the green laser light, and a UV laser light generating unit 112 for transforming the wavelength of the green laser light from the green laser light generating unit 111 to generate the UV laser light.

In the green laser light generating unit 111, a semiconductor laser 113 emits a high-output laser light with a wavelength $\lambda=808$ nm. This high output laser light is converged by a converging lens 114 to fall on a non-planar monolithic ring type Nd:YAG laser 115 as the exciting light which excites the Nd:YAG laser 115. This excites the Nd:YAG laser 115 to generate an IR laser light with a wavelength $\lambda=1064$ nm. At this time, an external magnetic field is applied to the Nd:YAG laser 115. This causes the Nd:YAG laser 115 to be oscillated only in one direction in the longitudinal simplex mode. The principle of the oscillation is disclosed in, for example, the U.S. Pat. No. 4,749, 842.

Here, the Nd:YAG laser 115 used is of the monolithic ring type. The monolithic ring type light resonator is high in oscillation stability and exhibits superior temporal coherence characteristics, as shown in T. Kane et al., Opt. Lett Vol.10 (1985), pp 65. On the other hand, the optical path in the resonator is preferably non-co-planar. If the optical path in the resonator is preferably non-co-planar, it is possible to render oscillations of the IR laser light more stable.

The IR laser light, radiated from the Nd:YAG laser 115, falls on a monolithic ring type MgO:LN crystal 117 through a mode matching lens 116. The MgO:LN crystal 117, on which falls the IR laser light with the wavelength $\lambda=1064$ nm, generates second harmonics with the wavelength $\lambda=532$ nm. This MgO:LN crystal 117 is designed to constitute a resonator with respect to the IR laser light with the wavelength $\lambda=1064$ nm. If the high power density in the resonator is utilized, high efficiency wavelength transformation can be realized with a continuous wave. Specifically, by forming the light resonator so that the wavelength of the IR laser light will be coincident with the oscillation wavelength in the interior of the MgO:LN crystal 117, the second harmonics can be generated with an efficiency as high as approximately 65%.

By generation of the second harmonics by the MgO:LN crystal 117, the green laser light, with the wavelength $\lambda=532$ nm, obtained on wavelength transformation of the IR laser light with the wavelength $\lambda=1064$ nm, is reflected by a light reflecting mirror 118 and shaped to a pre-set beam diameter by a lens 119 to exit the green laser light generating unit 111.

In the green laser light generating unit 111, configured as described above, the green laser light having superior temporal coherence can be generated with extremely high efficiency. If, in the green laser light generating unit 111, the laser light of 1 W is to be radiated from the semiconductor laser 1113, the IR laser light of the order of 500 mW is generated from the Nd:YAG laser 115, whilst the green laser light of the order of 200 mW is generated by the MgO:LN crystal 117. That is, the green laser light generating unit 111 has an extremely high efficiency. Moreover, the semiconductor laser 113 has an electrical efficiency higher than that of the gas laser and is approximately 30%. So, if the power consumption by e.g., a control circuit, is taken into consideration, the power consumption by the green laser light generating unit 111 is reduced appreciably.

The green laser light, generated by the green laser light generating unit 111, as described above, is incident on a UV laser light generating unit 112. The UV laser light generating unit 112 generates second harmonics of the green laser light, using a $\beta$-BaB$_2$O$_4$, referred to below as BB 121, as a non-linear optical component, to generate a UV laser light of the wavelength $\lambda=266$ nm. That is, the UV laser light generating unit 112 generates the UV laser light by BBO 121, as second harmonics, with the green laser light as a fundamental wave.

The BBO 121, transmitting the light up to a far ultraviolet range of the wavelength of 190 nm, invulnerable against laser damage and high in birefringence, is able to generate second harmonics over a wide wavelength range, and is optimum as an element for generating second harmonics in the far ultraviolet range. However, if the second harmonics of the wavelength $\lambda=266$ nm are to be generated by the BBO 121, angular phase matching is required, whilst temperature phase matching, such as is used in the MgO:LN crystal 117, cannot be used. Therefore, it is extremely difficult to generate second harmonics using a monolithic ring type crystal as in the case of the green laser light generating unit 111.

Therefore, the UV laser light generating unit 112 uses a ring type light resonator 126 provided with four independent mirrors 122 to 125 to generate second harmonics with the external resonation type.

The fundamental wave, incident on the UV laser light generating unit 112, that is the green laser light, is incident on the light resonator 126 through a phase modulator 127 and a mode matching lens 118. It is noted that the light resonator 126 is made up of the first to fourth mirrors 122 to 125, and that the BBO 121 is interposed between the first mirror 122 and the second mirror 123.

The fundamental wave is introduced into the light resonator 126 through the first mirror 122. A portion of the fundamental wave is reflected by the first mirror 122 and further reflected by the mirror 129 towards a photodetector 130 for detection thereby. On the other hand, the light transmitted through the first mirror 122 and introduced into the interior of the light resonator 126 is directed first by the BBO 121 towards the second mirror 123 so as to be reflected thereby towards the third mirror 124 so as to be thereby reflected towards the fourth mirror 125. The light is then reflected back by the fourth mirror 125 towards the first mirror 122 and reflected thereby so as to be re-directed through the BBO 121 towards the second mirror 123.

The fundamental wave, reflected by the first mirror 122 of the light resonator 126, is detected by the photodetector 130, as described above. The detection signal, obtained on detecting the fundamental wave, reflected by the first mirror 122 of the light resonator 126, by the photodetector 130, is sent to the control circuit 131. In the UV laser light generating unit 112, the phase modulator 127 phase-modulates the fundamental wave, incident on the light resonator 126, by the modulated signal from a phase modulator driving circuit 128. The control circuit 131 detects the detection signal in synchronism with the modulated signal to detect an error signal of the optical path phase difference of the light resonator 126, and drives an electromagnetic actuator 132, based on the error signal, so that the resonator length of the light resonator 126 will perpetually satisfy the conditions of resonation, thereby controlling the position of the third mirror 124 continuously and accurately.

By continuously and accurately controlling the position of the third mirror 124 as described above, the resonator length of the light resonator 126 can be controlled to an extremely high accuracy of the order of several hundredths of the light wavelength, even if the light resonator 126 is made up of independent plural mirrors 122 to 125. By precisely controlling the resonator length of the light resonator 126 to satisfy the resonation conditions at all times, the second harmonics can be generated by the BBO 121 extremely efficiently.

In the light resonator 126, an anti-reflection film is provided on the BBO 121 for diminishing the resonator loss. In addition, high reflectance mirrors, with the reflectance of the order of 99.9%, are used as the second to fourth mirrors 123 to 125 making up the light resonator 126. By providing an anti-reflection film on the BBO 121 and by employing high reflectance mirrors with the reflectance of the order of 99.9%, as the second to fourth mirrors 123 to 125, the resonator loss of the light resonator 126 can be suppressed to approximately 0.5% or less.

With the above-described UV laser light generating unit 112, the UV laser light, having superior temporal coherence characteristics, can be generated to an extremely sigh efficiency. In actuality, it has been confirmed that, when the UV laser light is generated by the UV laser light generating unit 112, with the output of 200 mW of the green laser light incident from the green laser light generating unit 111 to the UV laser light generating unit 112, the UV laser light of the order of 50 mW is obtained.

Meanwhile, the UV light has a high photon energy, so that, if the UV laser light is generated by generating the second harmonics by a BBO arranged in the light resonator, the mirrors or the BBO making up the light resonator tend to be deteriorated. So, the light source, configured for generating the UV laser light by generation of second harmonics by the BBO arranged in the light resonator, tends to be short in useful life or in reliability and hence cannot be practically used as light source for measurement instruments.

However, the present inventors have confirmed that, by improving BBO crystal growth or the anti-reflection film provided on the BBO, and optimizing the spot size of the light incident on the BBO, rinsing of the interior of the light resonator or the atmosphere, sufficient reliability and useful life can be assured even if second harmonics are generated by the BBO 121 provided within the light resonator 126, as shown in FIG. 8. Specifically, by the improvement and optimization, as discussed above, stable operations for not less than 1000 hours is assured if the UV laser light of 100 mW is generated, whilst stable operations for not less than 5000 hours is assured if the UV laser light of 30 mW is generated. From these results, it may be presumed that the useful life in case of generating the UV laser light of 20 mW may reach even 1000 hours. With this order of magnitude of the durability, the light source may be handled substantially as a maintenance-free light source, such that the light source may safely be used practically as a light source for an inspection apparatus.

The UV laser light, generated by the UV laser light generating unit 112, as described above, is collimated by a collimator lens 133 and beam-shaped by an anamorphic prism pair 134 to exit from a UV laser light source 138. Meanwhile, the anamorphic prism pair 134 executes beam shaping so that the spot of the UV laser light radiated from a UV laser light source 138 will be substantially circular in profile. The UV laser light, radiated by the light resonator 126, is an elliptically-shaped beam due to the walk-off effect by birefringence of the BBO 121. So, in this UV laser light source 138, the laser light is beam-shaped by the anamorphic prism pair 134 until the spot is substantially circular in profile, after which the UV laser light is radiated.

In the laser light source for UV light 38, the laser light from a solid laser light source (Nd:YAG laser 115) is subjected to two-stage wavelength transformation by generation of second harmonics employing non-linear optical elements (MgO: LN crystal 117 and BBO 121) to generate UV laser light. That is, the present UV laser light source 138 operates as a full-solid UV laser light source 138 generating the UV light solely by a solid element.

By constructing the UV laser light source 138 solely by a solid element, it is possible to realize a light source of a small size, high efficiency, low power consumption, high stability and high beam quality. Moreover, with the UV laser light source 138, there may be obtained a UV laser light having superior temporal coherence.

As the laser light source for generating the UV laser light, there are gas lasers, for example, excimer laser or argon laser. These gas lasers suffer from the problems that the apparatus is bulky in size, poor in efficiency and high in power consumption. For example, with an argon laser, oscillated with an wavelength of 351 nm, the efficiency is usually 0.001% or less. Conversely, with the laser light source for UV light 38, designed as the all-solid element, the efficiency is much higher, whilst the apparatus may be reduced in size appreciably.

In the case of the argon laser, there is also a problem that a large quantity of cooling water is required. Since oscillations are produced on circulation of cooling water, an argon laser, which is in need of a large quantity of cooling water, is not suited to inspection of a fine structure. Moreover, an argon laser suffers from a problem that it is poor in oscillation wavelength stability. In the case of an excimer laser, it is necessary to furnish a fluoride gas which is a dangerous substance. In addition, the excimer laser, generating pulses with high peak power, is not suited as a light source of the inspection device 1 which performs the inspection by photographing an image of the semiconductor wafer.

Conversely, the laser light source for UV light 38, generating the UV laser light by wavelength transformation of the laser light from the solid laser light source, overcomes the problems presented with the use of the gas laser, such as excimer laser or the gas laser.

The operational sequence in case of inspecting the semiconductor wafer by the inspection device 1 is explained by referring to the flowchart of FIGS. 9 to 12. Meanwhile, in the flowchart shows in FIGS. 9 to 12, the operational sequence as from the time the semiconductor wafer to be inspected is installed on the inspection stage 11. It is assumed that a large number of similar device patterns are formed on the semiconductor wafer, and that detection and classification of defects is carried out by photographing an image of an area where the defect exists (defect image) and an image of the remaining area (reference image) and by comparing the images.

Figure 9:
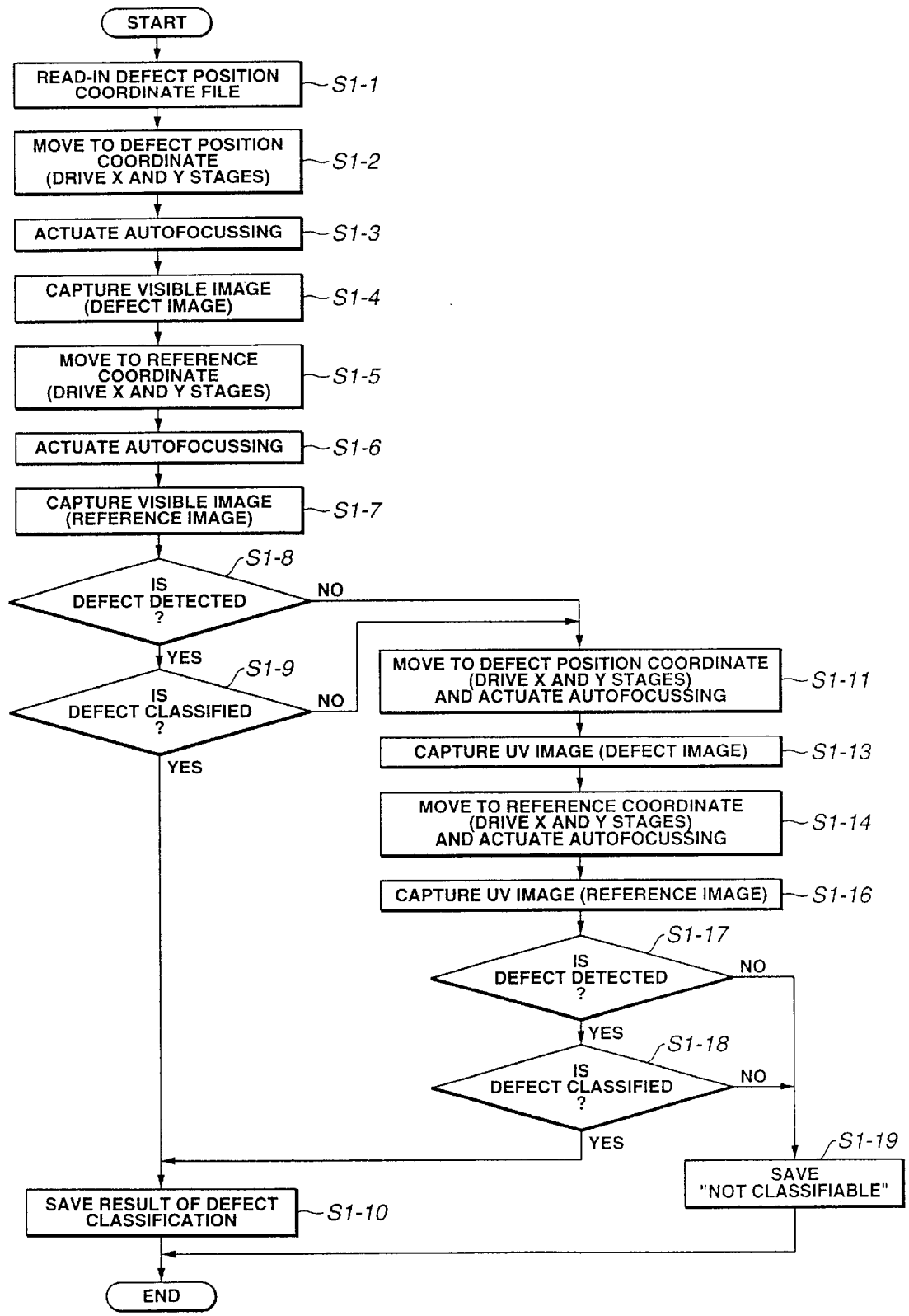
FIG. 9 is a flowchart showing a typical operational sequence in inspecting a semiconductor wafer by the inspection device according to the present invention.

First, the sequence of operations in inspecting the semiconductor wafer is explained in accordance with the flowchart of FIG. 9. Meanwhile, the flowchart of FIG. 9 shows a typical sequence of operations in inspecting on the semiconductor wafer by the inspection device 1 and classifying the inspected defects in case the positions of the defects are known from the outset.

In this case, a defective position coordinate file is read into the control computer 31, as shown at step S1-1. It is noted that the defective position coordinate file is a file stating the information on the positions of defects on the semiconductor wafer and which is prepared on previously measuring the positions of the defects on the semiconductor wafer by e.g., a defect detection device. Here, the defective position coordinate file is read into the control computer 31.

Then, at step S1-2, the X-stage 14 and the Y-stage 15 are driven by the control computer 31 to shift the semiconductor wafer to the defect position coordinate indicated by the defective position coordinate file so that the area of the semiconductor wafer under inspection will be in the field of view of the objective lens for visible light 36.

Then, at step S1-3, the auto-focussing unit for visible light 37 is driven by the control computer 31 to effect auto-focussing of the objective lens for visible light 36.

Next, at step S1-4, an image of the semiconductor wafer is photographed by the CCD camera for visible light 32 and the visible image as photographed is forwarded to the image-processing computer 30. Meanwhile, the visible image as photographed is an image at a defect position coordinate indicated by the defect position coordinate file, that is an image of the area where the defect is presumed to exist. This image is referred to below as a defect image.

Then, at step S1-5, the X-stage 14 and the Y-stage 15 are driven by the control computer 31 to shift the semiconductor wafer to the reference position coordinate so that the reference area of the semiconductor wafer will be in the field of view of the objective lens for visible light 36. It is noted that the reference area is an area of the semiconductor wafer other than the area to be inspected, that is an area in which a device pattern similar to the device pattern in the area under inspection of the semiconductor wafer.

Then, at step S1-6, the auto-focussing unit for visible light 37 is driven by the control computer 31 to effect auto-focussing of the objective lens for visible light 36.

Then, at step S1-7, an image of the semiconductor wafer is photographed by the CCD camera for visible light 32, and the visible image as photographed is routed to the image-processing computer 30. It is noted that the visible image as photographed here is an image of an area where there is formed a device pattern similar to the device pattern in the area under inspection of the semiconductor wafer. This image is referred to below as a reference image.

Next, at step S1-8, the defective image retrieved at step S1-4 is compared to the reference image retrieved at step S1-7 to find a defect from the defect image. If a defect is found, the processing transfers to step S1-9 and, if otherwise, the processing transfers to step S1-11.

At step S1-9, the image-processing computer 30 scrutinizes into the nature of the defect as found to proceed to classification. If defect classification has been completed, the processing transfers to step S1-10 and, if otherwise, the processing transfers to step S1-11.

At step S1-10, the results of classification of defects are saved. It is noted that the results of classification of defects are saved in a storage device connected to the image-processing computer 30 or to the control computer 31. Meanwhile, the results of classification of defects may also be transferred to and saved in another computer connected to the image-processing computer 30 or the control computer 31 over a network.

If the processing at step S1-10 has come to an end, the classification of defects of the semiconductor wafer comes to a close, so the processing is terminated. However, if there are plural defects on the semiconductor wafer, the program may revert to step S1-2 to detect and classify other defects.

If no defect has been found at step S108, or if the defect has not been classified at step S1-9, the processing transfers to step S1-11 ff., to effect imaging at a higher resolution using UV light to find and classify the defects.

In such case, the X-stage 14 and the Y-stage 15 are driven at step S1 to S11 to shift the semiconductor wafer to the defect position coordinate indicated by the defect position coordinate file so that the area under inspection of the semiconductor wafer will be in the field of view of the objective lens for UV light 40. Simultaneously, the Z-stage 17 is shifted, based on the distance detected by the distance sensor 41, to effect auto-focussing at the defect position coordinate. The processing contents of the coordinate shifting operations and auto-focussing operations at this step S1-11 will be explained in detail subsequently.

Then, at the step S1-13, an image of the semiconductor wafer is photographed by the CCD camera for UV light 33 to send the UV image as photographed to the image-processing computer 30. Meanwhile, the UV image as photographed is an image in the defect position coordinate indicated by the defect position coordinate file. It is noted that the defect image is photographed using the UV light shorter in wavelength than the visible light and at a higher resolution than with the use of the visible light.

Then, at step S1-14, the X-stage 14 and the Y-stage 15 are driven to shift the semiconductor wafer to a reference position coordinate to cause the reference area of the semiconductor wafer to enter the field of view of the objective lens for UV light 40. On the other hand, the auto-focussing at this reference position coordinate is effected by driving the Z-stage 17 based on the distance as detected by the distance sensor 41. Meanwhile, the processing contents of the coordinate shifting operations and auto-focussing operations at this step S1-11 will be explained in detail subsequently.

The reference area is an area other than the area under inspection of the semiconductor wafer, and an area where there is formed a device pattern similar to the device pattern in the area under inspection of the semiconductor wafer.

Next, at step S1-15, an auto-focussing controller for UV light 41 is driven by the control computer 31 to effect auto-focussing of the objective lens for UV light 40.

Then, at step S1-16, an image of the semiconductor wafer is photographed by the CCD camera for UV light 33 to send the UV image as photographed to the image-processing computer 30. It is noted that the UV image photographed here is an image of an area of the semiconductor wafer where there is formed a device pattern similar to the device pattern in the area under inspection of the semiconductor wafer. That is, the UV image is the reference image. Here, the reference image is photographed using the UV light, shorter in wavelength than the visible light, at a higher resolution than in case of employing the visible light.

Next, at step S1-17, the defect image retrieved at step S1-13 is compared to the reference image retrieved at step S1-16, by the image-processing computer 30, to find the defect from the defect image. If a defect has been found, the processing transfers to step S1-18 and, if otherwise, the processing transfers to step S1-19.

At step S1-18, the image-processing computer 30 scrutinizes into the nature of the defect as detected to proceed to classification. If the defect has been classified, the processing transfers to step S1-10 to save the classified results of the defects. If the defect has not been classified, the processing transfers to step S1-19.

At step S1-19, the information indicating the effect of failure in the defect classification is saved. The information indicating the effect of failure in classifying the defects is saved e.g., in a storage device connected to the control computer 31 or the image-processing computer 30. Meanwhile, this information may be transferred to and saved in a different computer connected over a network to the control computer 31 or the image-processing computer 30.

By the above-described procedure, the image photographed by the CCD camera for visible light 32 is processed and analyzed to inspect the semiconductor wafer at a low resolution. If it has not been possible to detect or classify the defects with the visible light, an image photographed by the CCD camera for UV light 33 is processed and analyzed to inspect the semiconductor wafer at a higher resolution. By so doing, finer defects can be detected and classified than is possible in case of detecting and classifying the defects using only the visible light.

However, if the visible light is used to effect imaging at a low resolution, the area that can be imaged at a time is wider. So, if the defect is larger in size sufficiently, it is preferred to inspect the semiconductor wafer using the visible light at low resolution for higher efficiency. Consequently, the semiconductor wafer can be inspected more efficiently by initially inspecting and classifying the defects, using the visible light, as discussed above, rather than detecting and classifying the defects using the UV light.

Figure 10:
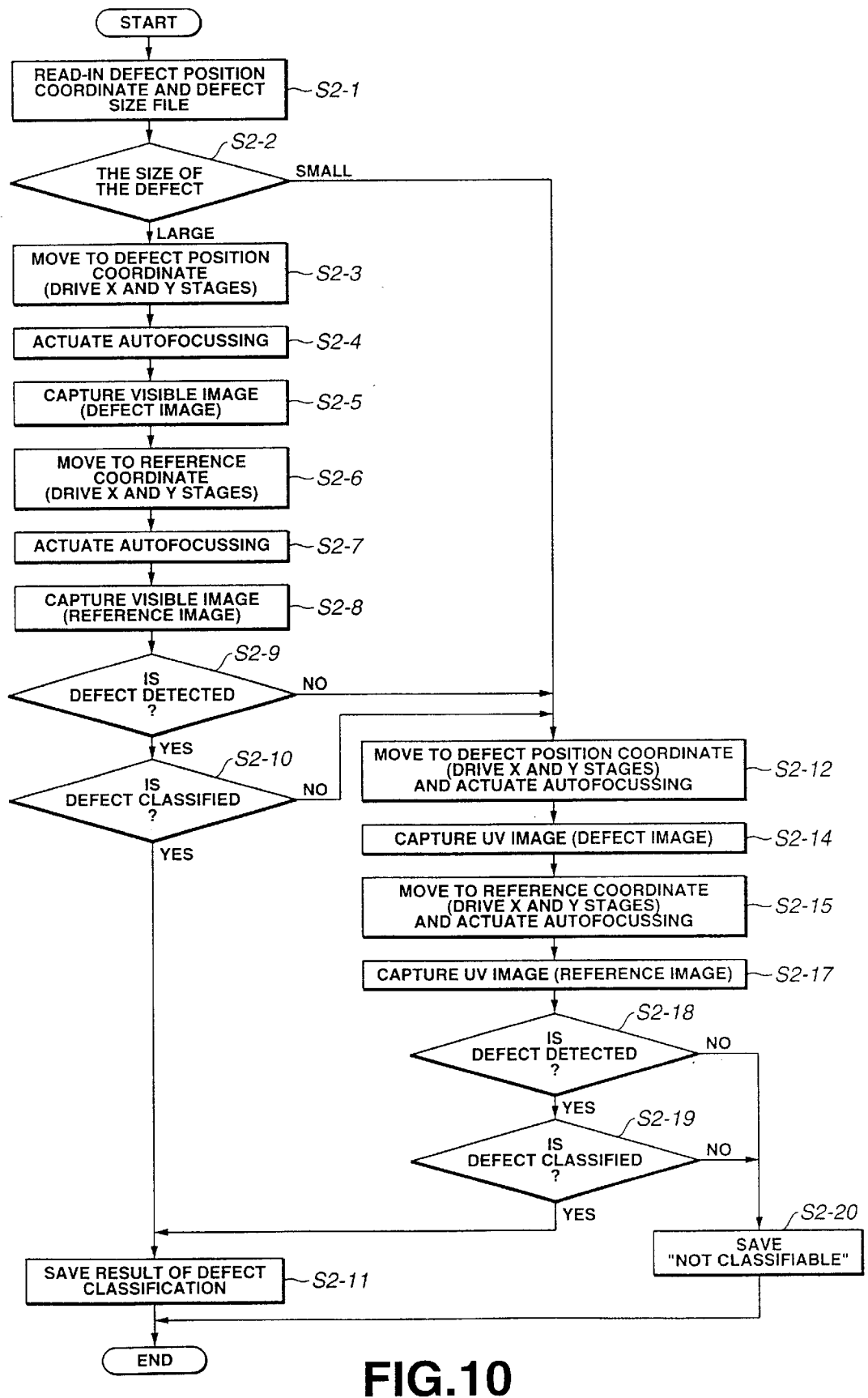
FIG. 10 is a flowchart showing another typical operational sequence in inspecting a semiconductor wafer by the inspection device according to the present invention.

The operational sequence in inspecting a semiconductor wafer in accordance with the flowchart of FIG. 10 is hereinafter explained. Meanwhile, the flowchart shown in FIG. 10 illustrates a typical operational sequence of inspecting and classifying the defects by the inspection device 1 when the position and the size of the defect on the semiconductor wafer are known at the outset.

In such case, the file of the defect position coordinate and the defect size is read into the control computer 31, as indicated at step S2-1. It is noted that the file of the defect position coordinate and the defect size is such a file stating the information on the defect position on the semi conductor wafer and the information on the defect size, and is prepared based on the position and the magnitude of the defects on the semiconductor wafer measured at the outset by e.g., a defect detection device. Here, the file is read into the control computer 31.

Next, at step S2-2, the size of the defect of the object of illumination is verified, based on the file read at step S2-1. If the size is larger than the pre-set size, the program moves to step S2-3 and, if otherwise, the program moves to step S2-12.

Meanwhile, the defect size is verified with the resolution for imaging with the UV light as a reference. If, with the diameter A of the defect of the object of illumination, the wavelength $\lambda$ of the UV light radiated from the laser light source for UV light 38 and with the numerical aperture NA of the objective lens for UV light 40, $A \geq 2 \times \lambda/NA$, the program moves to step S2-3 and, if $A < 2 \times \lambda/NA$, the program moves to step S2-12.

If, for example, $\lambda = 0.266\,\mu m$ and $NA=0.9$, $A=0.6\,\mu m$. This magnitude corresponds to the spot size of the visible light. Therefore, this magnitude corresponds to the threshold in case of executing defect inspection using the visible light. Stated differently, with a defect smaller than this magnitude, the defect detection ratio is appreciably lowered with defect detection with visible light. On the other hand, the defect size is of a sufficient magnitude. It is therefore highly desirable that the defect size be classified with $2 \times \lambda/NA$ or its vicinity as the boundary. This classification of the defect size in the vicinity of $2 \times \lambda/NA$ is the result found out by the present inventors based on numerous experiments. By doing the classification in this manner, it is possible to inspect the defects efficiently and without overlooking regardless of the defect size.

At step S2-3, the X-stage 14 and the Y-stage 15 are driven by the control computer 31 to shift the semiconductor wafer to a defect position coordinate indicated by the defect position coordinate file so that the area under inspection of the semiconductor wafer will be in the field of view of the objective lens for visible light 36.

Next, at step S2-4, the auto-focussing unit for visible light 37 is driven by the control computer 31 to effect auto-focussing of the objective lens for visible light 36.

Then, at step S2-5, an image of the semiconductor wafer is photographed by the CCD camera for visible light 32, and the visible image as photographed is sent to the image-processing computer 30. Meanwhile, the visible image, photographed here, is an image at a defect position coordinate indicated by the defect position coordinate file, that is the defect image.

Next, at step S2-6, the X-stage 14 and the Y-stage 15 are driven by the control computer 31 to shift the semiconductor wafer to the reference position coordinate to cause the reference area of the semiconductor wafer to enter the field of view of the objective lens for visible light 36. Meanwhile, the reference area is an area of the semiconductor wafer other than the area being inspected, and is an area where there is formed a device pattern similar to the device pattern in the area under inspection of the semiconductor wafer.

Then, at step S2-7, the auto-focussing unit for visible light 37 is driven by the control computer 31 to effect auto-focussing of the objective lens for visible light 36.

Then, at step S2-8, an image of the semiconductor wafer is photographed by the CCD camera for visible light 32 to send the photographed visible image to the image-processing computer 30. Meanwhile, the visible image, photographed here, is an image of an area of the semiconductor wafer where there is formed a device pattern similar to the device pattern in the area under inspection of the semiconductor wafer, that is a reference image.

Next, at step S2-9, the defect image captured at step S2-5 is compared by the image-processing computer 30 to the reference image captured at step S2-5 to find out the defect from the defect image. If the defect has been found out, the program moves to step S2-10 and, if otherwise, the program moves to step S2-12.

At step S2-10, the nature of the defect as found out is checked by the image-processing computer 30 by way of performing the classification. If the defect has been classified the program moves to step S2-11 and, if otherwise, the program moves to step S2-12.

At step S2-11, the result of classification of the defects is saved. It is noted that the result of classification of the defects is saved in a storage device connected to the image-processing computer 30 or to the control computer 31. Meanwhile, the result of classification of defects may be transferred to and saved in another computer connected over a network to the image-processing computer 30 or to the control computer 31.

When the processing at step S2-11 comes to a close, the classification of defects of the semiconductor wafer has come to a close, so the processing is terminated. However, if there are plural defects on the semiconductor wafer, the program reverts to step S2-2 to effect detection and classification of the second and the following defects.

If the defect is found at step S2-2 to be smaller than a pre-set size, if the defect has not been found at step S2-9 or if the defect has not been classified at step S2-10, the program moves to step S2-12 ff., to effect imaging at a high resolution with the use of the UV light by way of performing detection and classification of defects.

In such case, the X-stage 14 and the Y-stage 15 are driven at step S2-12 to shift the semiconductor wafer to a defect position coordinate indicated by the defect position coordinate file to cause the area under inspection of the semiconductor wafer to enter the field of view of the objective lens for UV light 40. Simultaneously, the auto-focussing at this defect position coordinate is effected by driving the Z-stage 17 based on the distance as detected by the distance sensor 41. Meanwhile, processing contents of the coordinate position shifting and auto-focussing at this step S2-12 are explained in detail subsequently.

Next, at step S2-14, the image of the semiconductor wafer is photographed by the CCD camera for UV light 33. The UV image as photographed is sent to the image-processing computer 30. Meanwhile, the UV image as photographed is an image at a defect position coordinate indicated by the defect position coordinate file, that is the defect image. It is noted that the defect image is photographed, using the UV light as the light of a shorter wavelength than the wavelength of the visible light, at a resolution higher than in imaging with the visible light.

Then, at step S2-15, the X-stage 14 and the Y-stage 15 are driven to shift the semiconductor wafer to a reference position coordinate to cause the reference area of the semiconductor wafer to enter the field of view of the objective lens for UV light 40. Simultaneously, auto-focussing at the reference position coordinate is executed by driving the Z-stage 17 based on the distance as detected by the distance sensor 41. Meanwhile, processing contents of the coordinate movement operation and the auto-focussing operation at this step S2-15 will be explained in detail subsequently.

It is noted that the reference area is an area other than the area under inspection of the semiconductor wafer and is an area where there is formed a device pattern similar to the device pattern in the area under inspection of the semiconductor wafer.

Then, at step S2-16, the auto-focussing sensor for UV light 41 is driven by the control computer 31 to make auto-focussing of the objective lens for UV light 40.

Then, at step S2-17, the image of the semiconductor wafer is photographed by the CCD camera for UV light 33, and the UV image as photographed is sent to the image-processing computer 30. Meanwhile, the UV image, photographed here, is an image of an area where there is formed a device pattern similar to the device pattern in the area under inspection of the semiconductor wafer, that is a reference image. It is noted that the reference image is photographed, using the UV light as the light of a shorter wavelength than the wavelength of the visible light, at a resolution higher than in imaging with the visible light.

Next, at step S2-18, the defect image captured at step S2-14 is compared to the reference image retrieved at step S2-17, by the image-processing computer 30, to find the defect from the defect image. If a defect has been found, the processing transfers to step S2-19 and, if otherwise, the processing transfers to step S2-20.

At step S2-19, the image-processing computer 30 scrutinizes into the nature of the defect as detected to proceed to classification. If the defect has been classified, the processing transfers to step S2-11 to save the classified results of the defects. If the defect has not been classified, the processing transfers to step S2-20.

At step S2-20, the information indicating the effect of failure in the defect classification is saved. The information indicating the effect of failure in classifying the defects is saved e.g., in a storage device connected to the control computer 31 or the image-processing computer 30. Meanwhile, this information may be transferred to and saved in a different computer connected over a network to the control computer 31 or the image-processing computer 30.

If the defect size is known, smaller defects can be inspected from the outset at a high resolution, using the UV light, without performing the inspection by the visible light, thereby enabling inspection at a higher efficiency.

Figure 11:
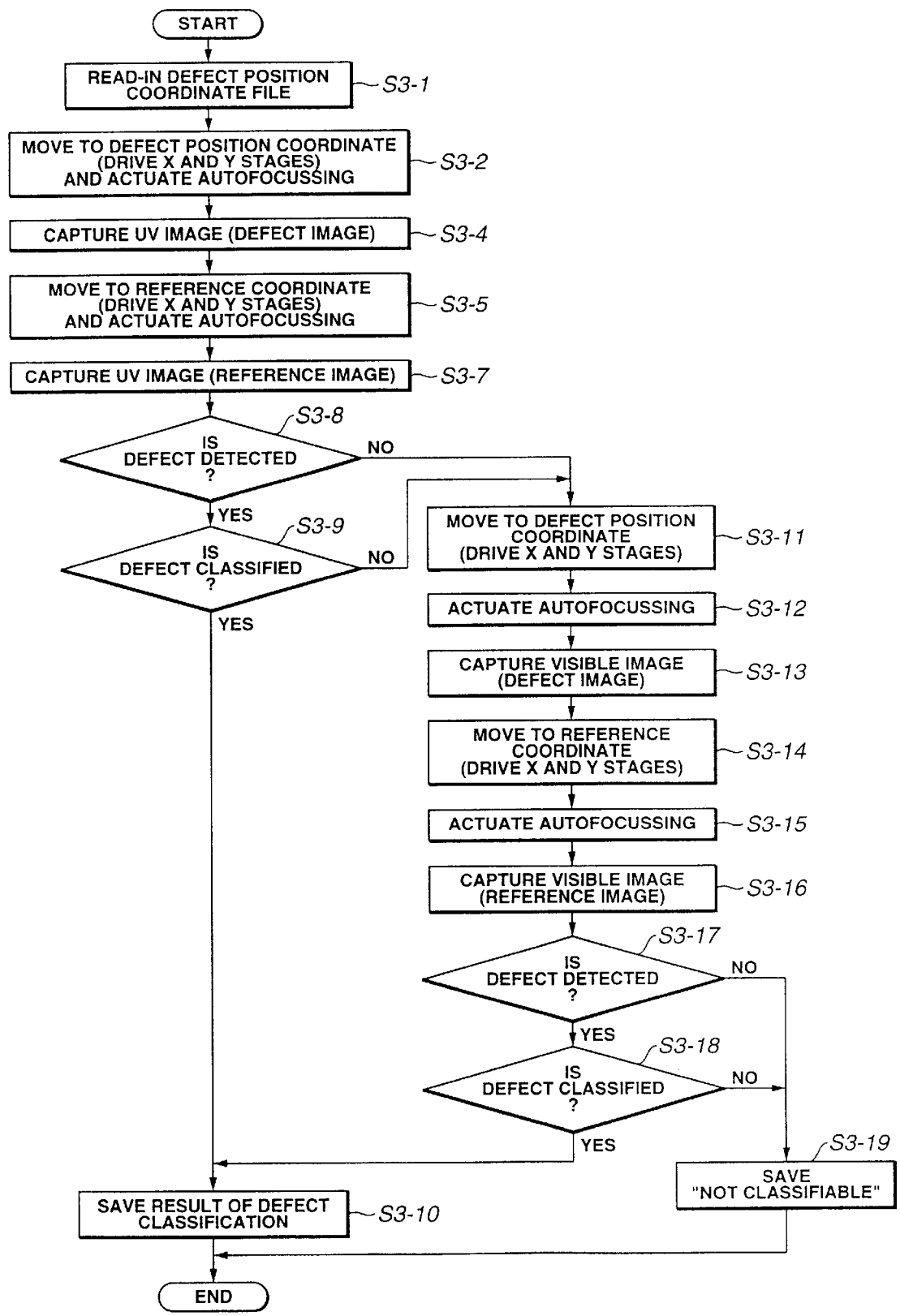
FIG. 11 is a flowchart showing still another typical operational sequence in inspecting a semiconductor wafer by the inspection device according to the present invention.

Referring to the flowchart of FIG. 11, the operational sequence in inspecting a semiconductor wafer is explained. Meanwhile, the flowchart shown in FIG. 11 shows an exemplary operating sequence in inspecting and classifying the defects on the semiconductor wafer by the inspection device 1 in case he defect positions on the semiconductor wafer are known at the outset.

In this case, the defect position coordinate file is initially read into the control computer 31, as indicated at step S3-1. It is noted that the defect position coordinate file is a file stating the information on defect positions on the semiconductor wafer, and is prepared based on positions of the defects on the semiconductor wafer as measured at the outset by e.g., a defect detection device. Here, the file is read into the control computer 31.

Then, at step S3-2, the X-stage 14 and the Y-stage 15 are driven to shift the semiconductor wafer to a reference position coordinate indicated by the defect position coordinate file to cause the reference area of the semiconductor wafer to enter the field of view of the objective lens for UV light 40. Simultaneously auto-focussing at the defect position coordinate is executed by driving the Z-stage 17 based on the distance as detected by the distance sensor 41. Meanwhile, processing contents of the coordinate movement operation and the auto-focussing operation at this step S3-2 will be explained in detail subsequently.

Next, at step S3-4, the image of the semiconductor wafer is photographed by the CCD camera for UV light 33. The UV image as photographed is sent to the image-processing computer 30. Meanwhile, the UV image as photographed is an image at a defect position coordinate indicated by the defect position coordinate file, that is the defect image.

Then, at step S3-5, the X-stage 14 and the Y-stage 15 are driven to shift the semiconductor wafer to a reference position coordinate to cause the reference area of the semiconductor wafer to enter the field of view of the objective lens for UV light 40. Simultaneously, the auto-focussing at the reference position coordinate is executed by driving the Z-stage 17 based on the distance as detected by the distance sensor 41. The processing contents of the coordinate movement operation and the auto-focussing operation at this step S2-15 will be explained in detail subsequently.

Then, at step S3-7, the image of the semiconductor wafer is photographed by the CCD camera for UV light 33, and the UV image as photographed is sent to the image-processing computer 30. Meanwhile, the UV image, photographed here, is an image of an area where there is formed a device pattern similar to the device pattern in the area under inspection of the semiconductor wafer, that is a reference image.

Next, at step S3-8, the defect image captured at step S3-4 is compared to the reference image retrieved at step S3-4, by the image-processing computer 30, to find the defect from the defect image. If a defect has been found, the processing transfers to step S3-9 and, if otherwise, the processing transfers to step S3-11.

At step S3-9, the image-processing computer 30 scrutinizes into the nature of the defect as detected to proceed to classification. If the defect has been classified, the processing transfers to step S3-10 to save the classified results of the defects. If the defect has not been classified, the processing transfers to step S3-11.

At step S3-10, the result of classification of defects is saved. Meanwhile, the result of classification of the defects is saved e.g., in a storage device connected to the image-processing computer 30 or to the control computer 31. Meanwhile, the result of classification of defects may be transferred to and saved in a different computer connected over a network to the control computer 31 or the image-processing computer 30.

When the processing at step S3-10 comes to a close, the classification of defects of the semiconductor wafer has come to a close, so the processing is terminated. However, if there are plural defects on the semiconductor wafer, the program reverts to step S3-2 to effect detection and classification of the second and the following defects.

If no defect has been found at step S3-8, or if the defect has not been classified at step S3-9, the processing transfers to step S3-11 ff., to effect imaging at a lower resolution using the visible light to find and classify the defects.

In such case, the X-stage 14 and the Y-stage 15 are driven by the control computer 31 at step S3-11 to shift the semiconductor wafer to a defect position coordinate indicated by the defect position coordinate file so that the area under inspection of the semiconductor wafer will be in the field of view of the objective lens for visible light 36.

Then, at step S3-12, the auto-focussing unit for visible light 37 is actuated by the control computer 31 to effect auto-focussing of the objective lens for visible light 36.

Then, at step S3-13, an image of the semiconductor wafer is photographed by the CCD camera for visible light 32 to send the visible image as photographed to the image-processing computer 30. Meanwhile, the visible image, photographed here, is an image at a defect position coordinate indicated by the defect position coordinate file, that is a defect image. It is noted that the defect image is photographed using the visible light, as the light of a longer wavelength than the UV light, at a resolution lower than in the case of employing the UV light.

Next, at step S3-14, the X-stage 14 and the Y-stage 15 are driven by the control computer 31 to shift the semiconductor wafer to the reference position coordinate to cause the reference area of the semiconductor wafer to enter the field of view of the objective lens for visible light 36. Meanwhile, the reference area is an area of the semiconductor wafer other than the area being inspected, and is an area where there is formed a device pattern similar to the device pattern in the area under inspection of the semiconductor wafer.

Then, at step S3-15, the auto-focussing unit for visible light 37 is driven by the control computer 31 to effect auto-focussing of the objective lens for visible light 36.

Then, at step S3-16, an image of the semiconductor wafer is photographed by the CCD camera for visible light 32 to send the photographed visible image to the image-processing computer 30. Meanwhile, the visible image, photographed here, is an image of an area of the semiconductor wafer where there is formed a device pattern similar to the device pattern in the area under inspection of the semiconductor wafer, that is a reference image. It is noted that the reference image is photographed at a resolution lower than with the use of the UV light, using the visible light as the light of a longer wavelength than the UV light.

Next, at step S3-17, the defect image captured at step S3-13 is compared to the reference image retrieved at step S3-16, by the image-processing computer 30, to find the defect from the defect image. If a defect has been found, the processing transfers to step S3-18 and, if otherwise, the processing transfers to step S3-19.

At step S3-18, the image-processing computer 30 scrutinizes into the nature of the defect as detected to proceed to classification. If the defect has been classified, the processing transfers to step S3-10 to save the classified results of the defects. If the defect has not been classified, the processing transfers to step S3-19.

At step S3-19, the information indicating the effect that the defect classification has failed is saved. The information indicating the effect of failure in classifying the defects is saved e.g., in a storage device connected to the control computer 31 or the image-processing computer 30. Meanwhile, this information may be transferred to and saved in a different computer connected over a network to the control computer 31 or the image-processing computer 30.

By the above-described procedure, a semiconductor wafer is inspected at a higher resolution by processing and analyzing an image photographed by the CCD camera for UV light 33 to inspect the semiconductor wafer at a higher resolution. If the defect detection or classification by the UV light is impossible, the semiconductor wafer is inspected at a lower resolution by processing and analyzing the image processed by the CCD camera for visible light 32. By so doing, it becomes possible to detect or classify finer defects than in case of detecting and classifying the defects using only the visible light.

Figure 12:
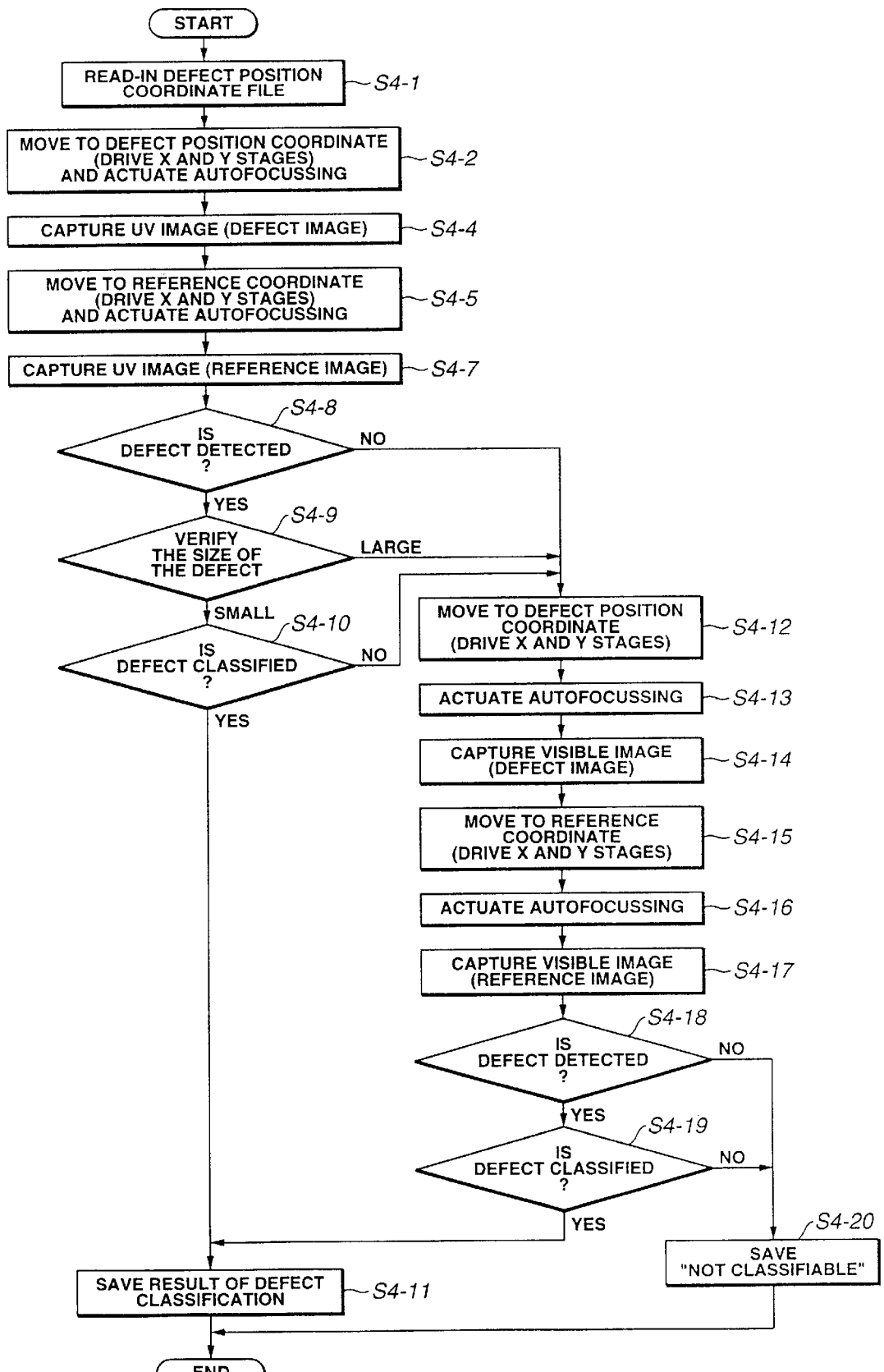
FIG. 12 is a flowchart showing yet another typical operational sequence in inspecting a semiconductor wafer by the inspection device according to the present invention.

Referring to the flowchart of FIG. 12, the processing of inspecting the semiconductor wafer is explained. Meanwhile, the flowchart of FIG. 12 shows an exemplary operating sequence in inspecting and classifying the defects on the semiconductor wafer by the inspection device 1 in case he defect positions on the semiconductor wafer are known at the outset.

In this case, the defect position coordinate file is initially read into the control computer 31, as indicated at step S4-1. It is noted that the defect position coordinate file is a file stating the information on the defect positions on the semiconductor wafer, and is prepared based on the positions of the defects on the semiconductor wafer as measured at the outset by e.g., a defect detection device. Here, the file is read into the control computer 31.

Then, at step S4-2, the X-stage 14 and the Y-stage 15 are driven to shift the semiconductor wafer to a defect position coordinate indicated by the defect position coordinate file to cause the area under inspection of the semiconductor wafer to enter the field of view of the objective lens for UV light 40. Simultaneously, auto-focussing at the defect position coordinate is executed by driving the Z-stage 17 based on the distance as detected by the distance sensor 41. Meanwhile, processing contents of the coordinate movement operation and the auto-focussing operation at this step S4-2 will be explained in detail subsequently.

Next, at step S4-4, the image of the semiconductor wafer is photographed by the CCD camera for UV light 33. The UV image as photographed is sent to the image-processing computer 30. Meanwhile, the UV image as photographed is an image at the defect position coordinate indicated by the defect position coordinate file, that is the defect image.

Then, at step S4-5, the X-stage 14 and the Y-stage 15 are driven to shift the semiconductor wafer to a reference position coordinate to cause the reference area of the semiconductor wafer to enter the field of view of the objective lens for UV light 40. Simultaneously, auto-focussing at the reference position coordinate is executed by driving the Z-stage 17 based on the distance as detected by the distance sensor 41. Meanwhile, processing contents of the coordinate movement operation and the auto-focussing operation at this step S4-15 will be explained in detail subsequently.

Meanwhile, the reference area is an area of the semiconductor wafer other than the area being inspected, and is an area where there is formed a device pattern similar to the device pattern in the area under inspection of the semiconductor wafer.

Then, at step S4-6, the auto-focussing unit for UV light 41 is driven by the control computer 31 to effect auto-focussing of the objective lens for UV light 40.

Then, at step S4-7, an image of the semiconductor wafer is photographed by the CCD camera for UV light 33 to send the photographed visible image to the image-processing computer 30. Meanwhile, the visible image, photographed here, is an image of an area of the semiconductor wafer where there is formed a device pattern similar to the device pattern in the area under inspection of the semiconductor wafer, that is a reference image.

Next, at step S4-8, the defect image captured at step S4-4 is compared to the reference image retrieved at step S4-7, by the image-processing computer 30, to find the defect from the defect image. If a defect has been found, the processing transfers to step S4-9 and, if otherwise, the processing transfers to step S4-12.

At step S4-9, the size of the defect as detected at step S4-8 is verified. If the defect is larger in size than the pre-set size, the program moves to step S4-12 and, if otherwise, the program moves to step S4-10.

Meanwhile, the defect size is verified with the resolution in case of imaging with the UV light as a reference. If, with the diameter A of the defect of the object of illumination, the wavelength X of the UV light radiated from the laser light source for UV light 38 and with the numerical aperture NA of the objective lens for UV light 40, $A \geq 2 \times \lambda/NA$, the program moves to step S4-12 and, if $A < 2 \times \lambda/NA$, the program moves to step S4-10.

If, for example, $\lambda=0.266 \mu m$ and $NA=0.9$, $A=0.6 \mu m$. This magnitude corresponds to the spot size of the visible light. Therefore, this magnitude corresponds to the threshold in case of executing defect inspection using the visible light. Stated differently, with a defect smaller than this magnitude, the defect detection ratio is appreciably lowered in case of defect detection with visible light. On the other hand, the defect size is of a sufficient magnitude in case the defect is to be inspected using the UV light. It is therefore highly desirable that the defect size be classified with $2 \times \lambda/NA$ or its vicinity as a boundary. This classification of the defect size in the vicinity of $2 \times \lambda/NA$ is the result found out by the present inventors based on numerous experiments. By doing the classification in this manner, it is possible to inspect the defects efficiently without overlooking regardless of the defect size.

At step S4-10, the nature of the detected defect is checked by the image-processing computer 30 to execute defect classification. If the defect has been classified, the program moves to step S4-11 and, if otherwise, the program moves to step S4-12.

At step S4-11, the result of classification of defects is saved. Meanwhile, the result of classification of the defects is saved e.g., in a storage device connected to the image-processing computer 30 or to the control computer 31. Meanwhile, the result of classification of defects may be transferred to and saved in a different computer connected over a network to the control computer 31 or the image-processing computer 30.

When the processing at step S4-11 comes to a close, the classification of defects of the semiconductor wafer has come to a close, so the processing is terminated. However, if there are plural defects on the semiconductor wafer, the program may revert to step S4-2 to effect detection and classification of the next and the following defects.

If no defect has been found at step S4-8, or if the defect has not been classified at step S4-9, the processing transfers to step S4-10 ff., to effect imaging at a lower resolution using the visible light to find and classify the defects.

In such case, the X-stage 14 and the Y-stage 15 are driven by the control computer 31 at step S4-12 to shift the semiconductor wafer to the defect position coordinate indicated by the defect position coordinate file so that the area under inspection of the semiconductor wafer will be in the field of view of the objective lens for visible light 36.

Then, at step S4-13, the auto-focussing unit for visible light 37 is actuated by the control computer 31 to effect auto-focussing of the objective lens for visible light 36.

Then, at step S4-14, an image of the semiconductor wafer is photographed by the CCD camera for visible light 32 to send the visible image as photographed to the image-processing computer 30. Meanwhile, the visible image, photographed here, is an image at a defect position coordinate indicated by the defect position coordinate file, that is a defect image. It is noted that the defect image is photographed using the visible light, as the light of a longer wavelength than the UV light, at a resolution lower than in the case of employing the UV light.

Next, at step S4-15, the X-stage 14 and the Y-stage 15 are driven by the control computer 31 to shift the semiconductor wafer to the reference position coordinate to cause the reference area of the semiconductor wafer to enter the field of view of the objective lens for visible light 36. Meanwhile, the reference area is an area of the semiconductor wafer other than the area being inspected, and is an area where there is formed a device pattern similar to the device pattern in the area under inspection of the semiconductor wafer.

Then, at step S4-16, the auto-focussing unit for visible light 37 is driven by the control computer 31 to effect auto-focussing of the objective lens for visible light 36.

Then, at step S4-17, an image of the semiconductor wafer is photographed by the CCD camera for visible light 32 to send the photographed visible image to the image-processing computer 30. Meanwhile, the visible image, photographed here, is an image of an area of the semiconductor wafer where there is formed a device pattern similar to the device pattern in the area under inspection of the semiconductor wafer, that is a reference image. It is noted that the reference image is photographed at a resolution lower than with the use of the UV light, using the visible light as the light of a longer wavelength than the UV light.

Next, at step S4-18, the defect image captured at step S4-18 is compared to the reference image retrieved at step S4-14, by the image-processing computer 30, to find the defect from the defect image. If a defect has been found, the processing transfers to step S4-19 and, if otherwise, the processing transfers to step S4-20.

At step S4-19, the image-processing computer 30 scrutinizes into the nature of the defect as detected to proceed to classification. If the defect has been classified, the processing transfers to step S4-11 to save the classified results of the defects. If the defect has not been classified, the processing transfers to step S4-20.

At step S4-20, the information indicating the effect of failure in the defect classification is saved. The information indicating the effect of failure in classifying the defects is saved e.g., in a storage device connected to the control computer 31 or the image-processing computer 30. Meanwhile, this information may be transferred to and saved in a different computer connected over a network to the control computer 31 or the image-processing computer 30.

By the above-described procedure, a semiconductor wafer is inspected at a higher resolution by processing and analyzing an image photographed by the CCD camera for UV light 33 to inspect the semiconductor wafer at a higher resolution. If the defect detection or classification by the UV light is impossible, the semiconductor wafer is inspected at a lower resolution by processing and analyzing the image processed by the CCD camera for visible light 32. By so doing, it becomes possible to detect or classify finer defects than is possible in case of detecting and classifying the defects using only the visible light. If the defect found out using the UV light is of a larger size, defect detection or classification is performed using the visible light, so the classification of a coarser size can be performed with higher precision.

Figure 13:
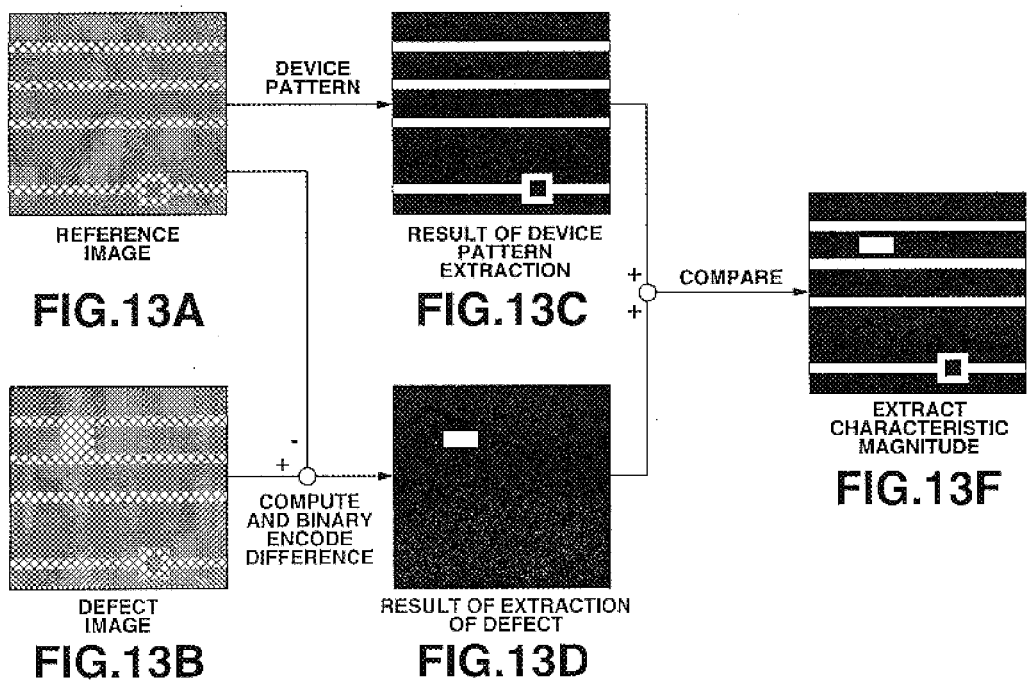
FIG. 13 illustrates a technique for defect detection from a reference image and a defect image.

Meanwhile, in the above-described inspection device 1, defects are found out from the reference and defect images photographed by the CCD cameras 32, 33. The technique of finding out defects from the reference and defect images in this manner is now explained with reference to FIG. 13.

FIG. 13a shows an example of an image of a reference area, carrying a device pattern similar to the device pattern in the area under inspection, that is a reference image, whilst FIG. 13b shows an example of an image of the area under inspection where a defect is presumed to exist, that is a defect image.

In detecting the defect from the reference and defect images, a device pattern is extracted from the reference image, based on the color information and the gray scale information, as shown in FIG. 13c. A difference image is also found from the reference and defect images and a portion with a larger difference is extracted as a defect, as shown in FIG. 13d.

Referring to FIG. 13f, an image then is obtained by superposing an image corresponding to the result of extraction of the device pattern, shown in FIG. 13c on an image corresponding to the result of extraction of the defect as shown in FIG. 13d, and e.g., the proportion of the defect present in the device pattern is extracted as the characteristic value concerning the defect.

In the inspection device 1, the reference and defect images, photographed by the CCD cameras 32, 33, are processed and analyzed by the image-processing computer 30 to find out a defect to inspect a semiconductor wafer.

The sequence of operations of shifting the objective lens for UV light 40 to the coordinate to be measured and of auto-focussing the objective lens for UV light 40, executed in inspecting the semiconductor wafer as described above, is now explained in further detail. Meanwhile, the following operations are associated with the operations of the steps S1-1 and S1-14 shown in FIG. 9, steps S2-12 and S2-15 shown in FIG. 10, steps S3-2 and S3-5 shown in FIG. 11 and steps S4-2 and S4-5 shown in FIG. 12.

In executing the operation of shifting the objective lens for UV light 40 to the coordinate to be measured and auto-focussing the objective lens for UV light 40, the X-stage 14 and the Y-stage 15 are actuated at step S5-1 by the control computer 31, so that the target illuminating position of the semiconductor wafer will be in the field of view of measurement by the distance sensor 41. That is, the semiconductor wafer is shifted horizontally to shift the distance sensor 41 onto the illumination target position.

Next, at step S5-2, the Z-stage 17 is actuated by the control computer 31, as the distance up to the semiconductor wafer is detected by the distance sensor 41, to bring the distance between the distance sensor 41 and the semiconductor wafer into coincidence with the target distance T. That is, the semiconductor wafer is shifted in the height-wise direction (perpendicular direction) until the output value of the distance sensor 41 is equal to the target distance T.

Then, at step S5-3, the X-stage 14 and the Y-stage 15 are actuated by the control computer 31 to cause the illumination target position of the semiconductor wafer to enter the field of view of the objective lens for UV light 40. That is, the semiconductor wafer is shifted in the horizontal direction to shift the objective lens for UV light 40 onto the illumination target position. At this time, the Z-stage 17 is not shifted, that is, the semiconductor wafer is not moved in the perpendicular direction.

The coordinate shifting operation to the coordinate to be measured and the auto-focussing at this coordinate to be measured may be achieved by the above-described sequence of operations. The illumination target position is imaged following this coordinate shifting and auto-focussing operations.

Meanwhile, the target distance T, adjusted at step S5-2, is set by the control computer 31 as follows:

Target distance $T=Ti+C1+C2+C3$ where
Ti fixed target value
C1: first correction value set in keeping with an XY coordinate of the inspection stage 11
C2: second correction value set in keeping with an XY coordinate on the semiconductor wafer
C3: third correction value set in keeping with the drift magnitude of the distance sensor 41

The fixed target value Ti is an initial setting distance between the distance sensor 41 and the semiconductor wafer. For this target value Ti, a distance corresponding to the focal length of the objective lens for UV light 40 is set. For example, an output issued from the distance sensor 41 when the focal point position of the objective lens for UV light 40 is coincident on the semiconductor wafer, placed completely parallel to the objective lens for UV light 40, is this fixed target value Ti.

This fixed target distance Ti is set at the time of shipment or initial setting of the inspection device 1. In setting this fixed target distance Ti, a reference semiconductor wafer, planarized sufficiently, is sucked onto the suction plate 18 of the inspection stage 11 (operating step 1). The X-stage 14 and the Y-stage 15 are actuated to shift a point of observation on the reference semiconductor wafer to directly below the objective lens for UV light 40 (operating step 2). Then, as the focal point position of the objective lens for UV light 40 is observed visually, the Z-stage 17 is shifted until the focal point position coincides with the reference semiconductor wafer (operating step 3). An output value of the distance sensor 41 at this time is read and memorized as the fixed target distance. It is possible to execute the above operations a number of times to use an average value as the fixed target distance Ti.

The control computer 31 revokes the fixed target distance Ti, as set at the time of shipment of initial setting of the inspection device 1, each time the coordinate of the objective lens for UV light 40 is to be shifted or the objective lens for UV light 40 is to be auto-focussed, in order to set the above target distance T.

Figure 15A:
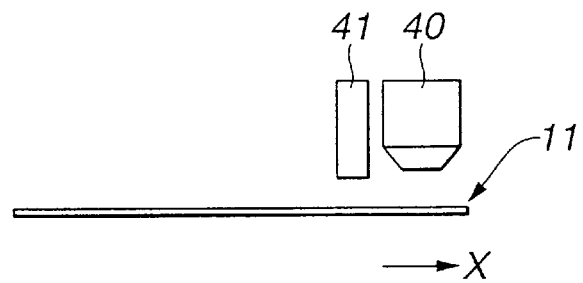
FIG. 15 illustrates the relation between the distance between the objective lens for UV light and the semiconductor wafer and the distance between the distance sensor and the semiconductor wafer in each movement position of the inspection stage.
Figure 15B:
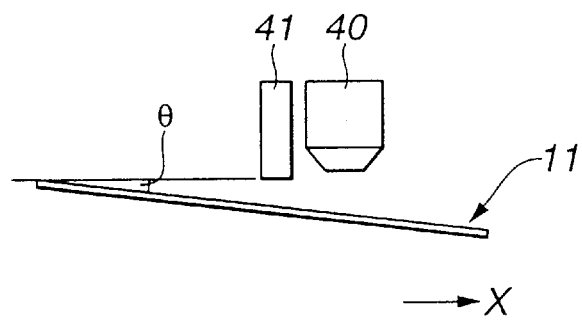
Figure 15C:
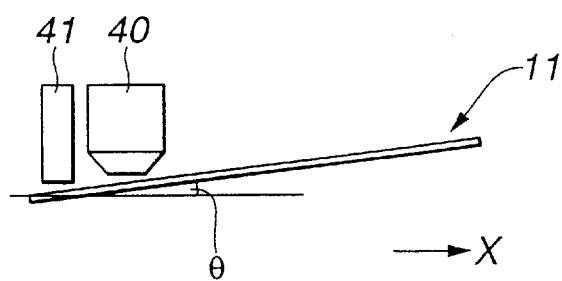

The first correction value C1 is a value for correcting the deviation of the fixed target value Ti produced due to, for example, tilt of the inspection stage 11. In this inspection device 1, the objective lens for UV light 40 and the distance sensor 41 are provided at a pre-set distance in the horizontal direction from each other. So, if the driving of the inspection stage 11 in the horizontal direction is subjected to tilt or distortion, the relative magnitudes of the "distance between the objective lens for UV light 40 and the semiconductor wafer" and the "distance between the distance sensor 41 and the semiconductor wafer" differ with shifting positions of the inspection stage 11. If, for example, the inspection stage 11 is horizontal with respect to the objective lens for UV light 40 at an end of the inspection stage 11 in the direction X, as shown in FIG. 15A, it may be an occurrence that the inspection stage 11 is tilted with respect to the objective lens for UV light 40 in the vicinity of the center of the inspection stage 11, as shown in FIG. 15B, or that the inspection stage 11 is tilted in the opposite direction with respect to the objective lens for UV light 40 at the opposite end in the direction X of the inspection stage 11, as shown in FIG. 15C. The first correction value C1 corrects the relative magnitudes of the "distance between the objective lens for UV light 40 and the semiconductor wafer" and the "distance between the distance sensor 41 and the semiconductor wafer", which differ with the shifting position of the inspection stage 11 in association with the shifting positions.

In setting this first correction value C1, a reference semiconductor wafer, planarized sufficiently, is sucked onto the suction plate 18 of the inspection stage 11 (operating step 11). The X-stage 14 and the Y-stage 15 are shifted in the directions X and Y in a matrix configuration at a pre-set pitch. As the focal point position of the objective lens for UV light 40 is observed visually at each matrix position, the focal point position is brought into coincidence with the reference semiconductor wafer (operating step 11). The fixed target distance Ti is subtracted from the output value of the distance sensor 41 at each position to give a difference value which is used as the first correction value C1. This first correction value C1 is associated with the XY coordinate to prepare a matrix-like table shown in FIG. 16 (operating step 12).

The control computer 31 at the above step S5-2 reads out the first correction value C1, associated with the XY coordinate of the illumination target position, from the matrix-like table, to find the target distance T. Meanwhile, this first correction value C1 is a inherent value of the inspection device 1. This first correction value C1 is set once at the time of shipment or initial setting of the inspection device 1 and is to be corrected periodically.

Figure 17:
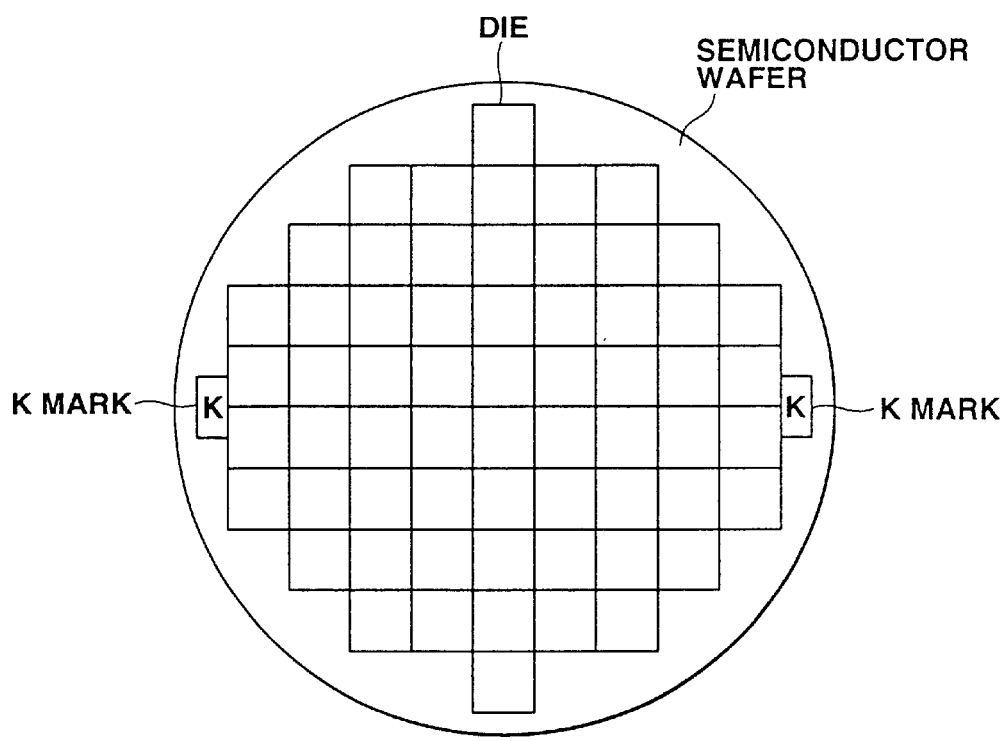
FIG. 17 illustrates a semiconductor wafer on which plural dies are formed.

The second correction value C2 is used for correcting the deviation of the fixed target distance Ti produced due to the step difference in the die in the semiconductor wafer. In a sole disc-shaped semiconductor wafer, plural rectangular dies of the same pattern, approximately 10 mm by 10 mm, are formed, as shown in FIG. 17. In a die where logics and a DRAM co-exist, there is produced a large step difference in the boundary between the logic portion and the DRAM portion, due to the difference in the pattern forming process. Depending on the pattern configuration, it may be an occurrence that the step difference in this boundary portion becomes larger than the depth of focus. In a capacitance type sensor, used as the distance sensor 41, the measurement field of view is usually of the order of 3 mm. The distance sensor 41 measures the average distance within this measurement field of view. Thus, if a step difference is present in the measurement field of view, it may be an occurrence that the distance up to the illumination target position cannot be measured accurately. This second correction value C2 corrects the height difference at each position in the die in association with respective positions in the die.

Figure 18:
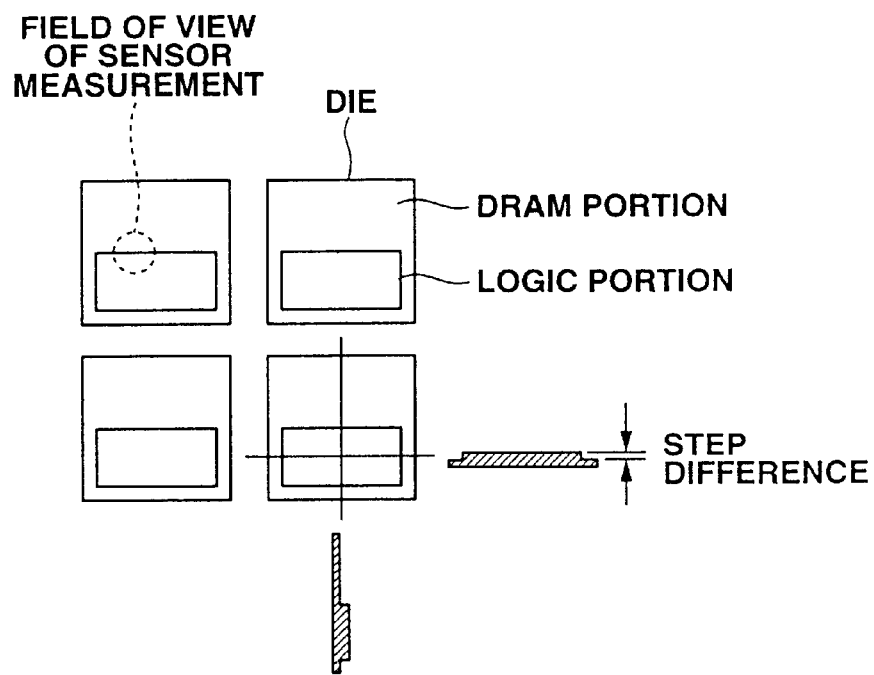
FIG. 18 illustrates the step difference formed in the die.

This second correction value C2 is set for each sort of the sem to be inspected, and is stored in the data file. In this data file, the height information corresponding to the XY coordinates in a die is stored as the second correction value C2. For example, the position in the die of shaded portions shown in FIG. 18 (logic portion) is stored, whilst the information to the effect that this shaded portion is higher than 1 μm than the remaining portion (DRAM portion)is stored as the second correction value C2. If this shaded portion is to be the illumination target position, this second correction value C2 is added to the fixed target distance Ti.

The control computer 31 at the above step S5-2 reads out the data file and sums the second correction value C2 to the pre-set target distance Ti depending on the illumination target position in the die to find the target distance T. Meanwhile, the second correction value C2 differs with the sort of the semiconductor wafer and is indicated by the coordinate in the die. Thus, at the time of starting the inspection of the semiconductor wafer, the inspection device 1 finds the relative position in the die, as reference points of the XY coordinate used in the inspection stage 11 and the XY coordinate on the semiconductor wafer are brought into coincidence with each other. Specifically, the coordinate on the semiconductor wafer is brought into coincidence with the shifting coordinate of the inspection stage 11 by detecting a so-called K-mark on the semiconductor wafer, which is a semiconductor wafer handling portion and indicates the reference position on the wafer.

A third correction value C3 is used for correcting an error produced due to drift of an output value caused by chronological changes of the distance sensor 41, such as temperature changes. For example, in the capacitance type sensor, used as the distance sensor 41, the sensor output value is changed with changes in the outside air temperature. Thus, if temperature changes occur in he inspection device 1, there is produced an error in the output value of the distance sensor, this error increasing in magnitude with lapse of time. The third correction value C3 eliminates the effect of the drift of the output value of the distance sensor 41.

In setting the third correction value C3, the reference semiconductor wafer, sufficiently planarized, is sucked onto the suction plate 18 of the inspection stage 11 (operating step 21). The X-stage 14 and the Y-stage 15 are then moved to shift the objective lens for visible light 36 to a pre-set measurement position on the semiconductor wafer to effect auto-focussing at this pre-set position. By performing the auto-focussing using the objective lens for visible light 36, the distance between the objective lens for UV light 40 and the semiconductor wafer is of a "certain known value". The X-stage 14 and the Y-stage 15 then are driven to shift the distance sensor 41 to the above-mentioned pre-set position to detect the sensor output at this time (operating step 23). The "sensor output" of "the known value" is found and the value so found is memorized as the third correction value C3. The above-described processing is carried out repeatedly to update the third correction value C3 each time. Meanwhile, the above operating steps 21 to 23 are carried out at the time of shipment or initial setting to find the "sensor output", which is of "the certain known value".

The control computer 31 at the above step S5-2 reads out the third correction value C3 to find the target distance T. This third correction value C3 is of a temporally changed value. So, the data of the third correction value C3 is found at the time of shipment or initial setting of the inspection device 1 and corrected subsequently at regular intervals.

Since the inspection device 1 uses the distance sensor 41, auto-focussing of the objective lens for UV light 40 may be carried out accurately, speedily and readily. Since the target distance T is corrected using the first to third correction values C1 to C3, auto-focussing can be achieved more accurately.

Meanwhile, the distance sensor 41 may be of any type provided that it is a non-contact type distance detection means capable of detecting the distance shorter than the depth of focus of the objective lens for UV light 40. So, the distance sensor 41 may be one employing optical means, such as laser Doppler meter, without being limited to the capacitance type sensor. However, a silicon oxide film is formed as an insulating film on the semiconductor wafer. Since silicon oxide transmits light, accurate distance detection is difficult if a distance sensor employing optical means is applied. Therefore, a capacitance type sensor not employing optical means is more preferred for an inspection device used for inspecting a semiconductor wafer.

Figure 19:
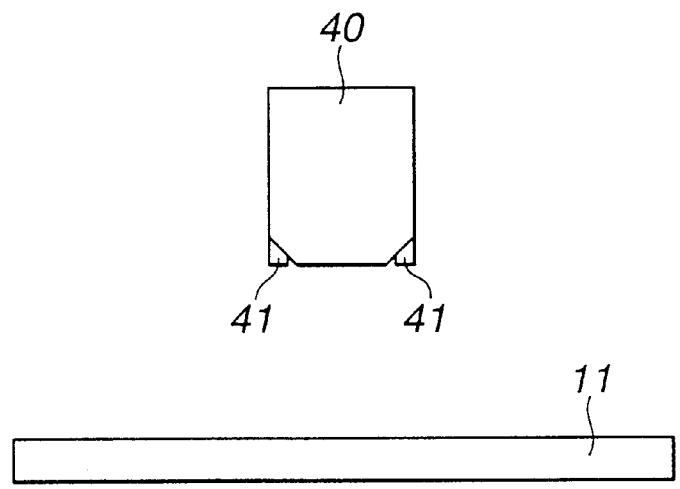
FIG. 19 illustrates a distance sensor mounted as one on an objective lens for UV light.

Recently, development of the small-sized capacitance type sensor is underway. So, a small-sized small-sized capacitance type sensor may be formed integrally with the objective lens for UV light 40, as shown in FIG. 19, in place of providing the distance sensor 41 at a pre-set separation from the objective lens for UV light 40 explained in connection with the inspection device 1. In this case, the field of view of the distance sensor 41 coincides with the objective lens for UV light 40. So, in the operation of shifting the objective lens for UV light 40 shown in FIG. 14 to the coordinate being measured, and in the auto-focussing operation, the operating step of causing the illumination target position of the semiconductor wafer to enter the field of view of the objective lens for UV light 40 at step 5-3 is unnecessary, whilst the first correction value C1 is unnecessary in finding the target distance T.

Figure 20:
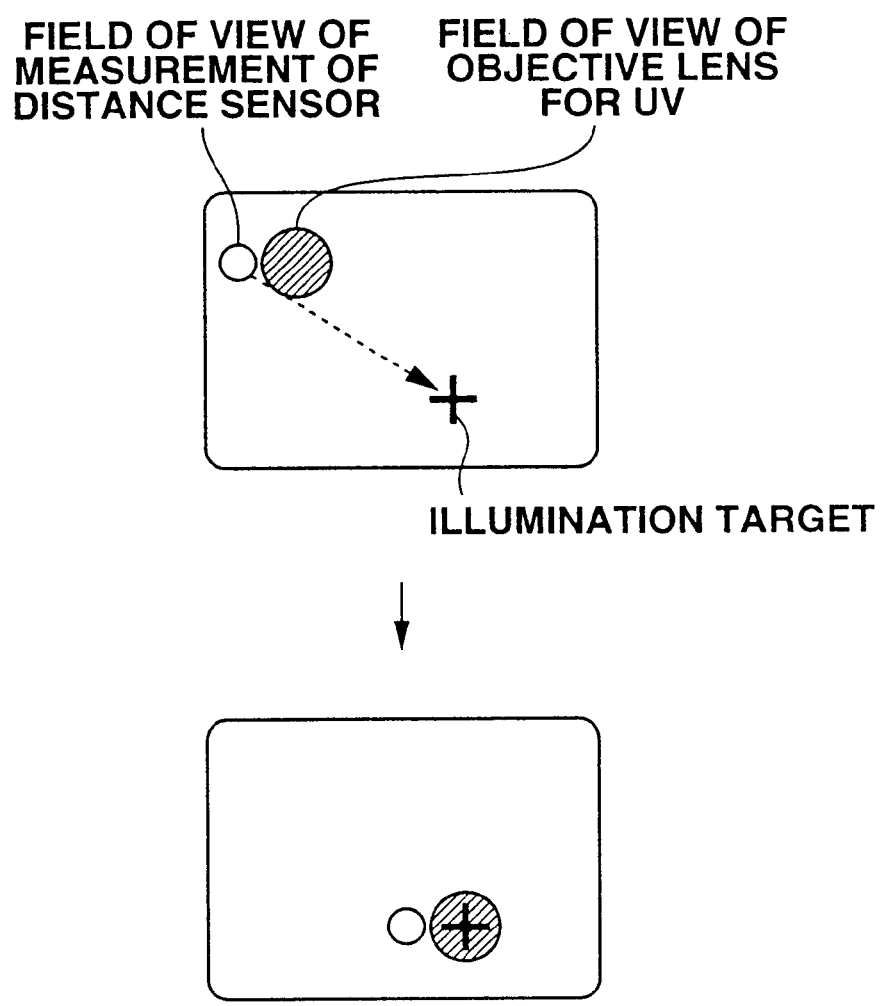
FIG. 20 illustrates the operation for auto-focussing by a distance sensor, with the objective lens for UV light being directly moved to the illumination target position.
Figure 21:
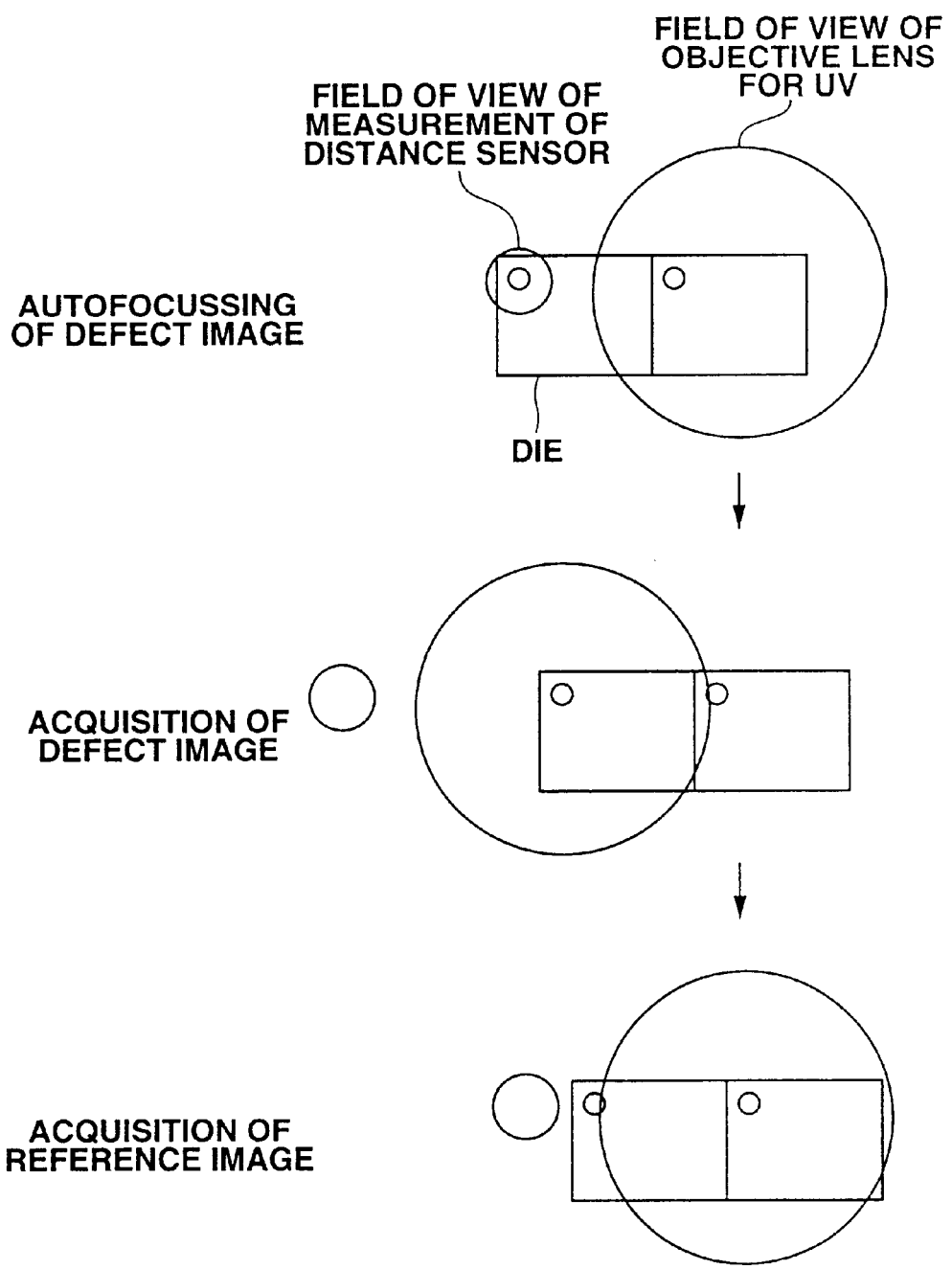
FIG. 21 illustrates the operation of directly moving the objective lens for UV light on the coordinate of the defect image to the coordinate for the reference image.

If the distance sensor 41 is not formed integrally with the objective lens for UV light 40, however, the distance between the objective lens for UV light 40 and the distance sensor 41 is sufficiently small or if the tilt of the inspection stage 11 is small, it is also possible to shift the objective lens for UV light 40 directly to the illumination target position to effect auto-focussing by the distance sensor 41 at this position, as shown in FIG. 20, in place of performing a two-step operation of shifting the distance sensor 41 to the illumination target position for focussing and subsequently shifting the objective lens for UV light 40 to the illumination target position.

Figure 14:
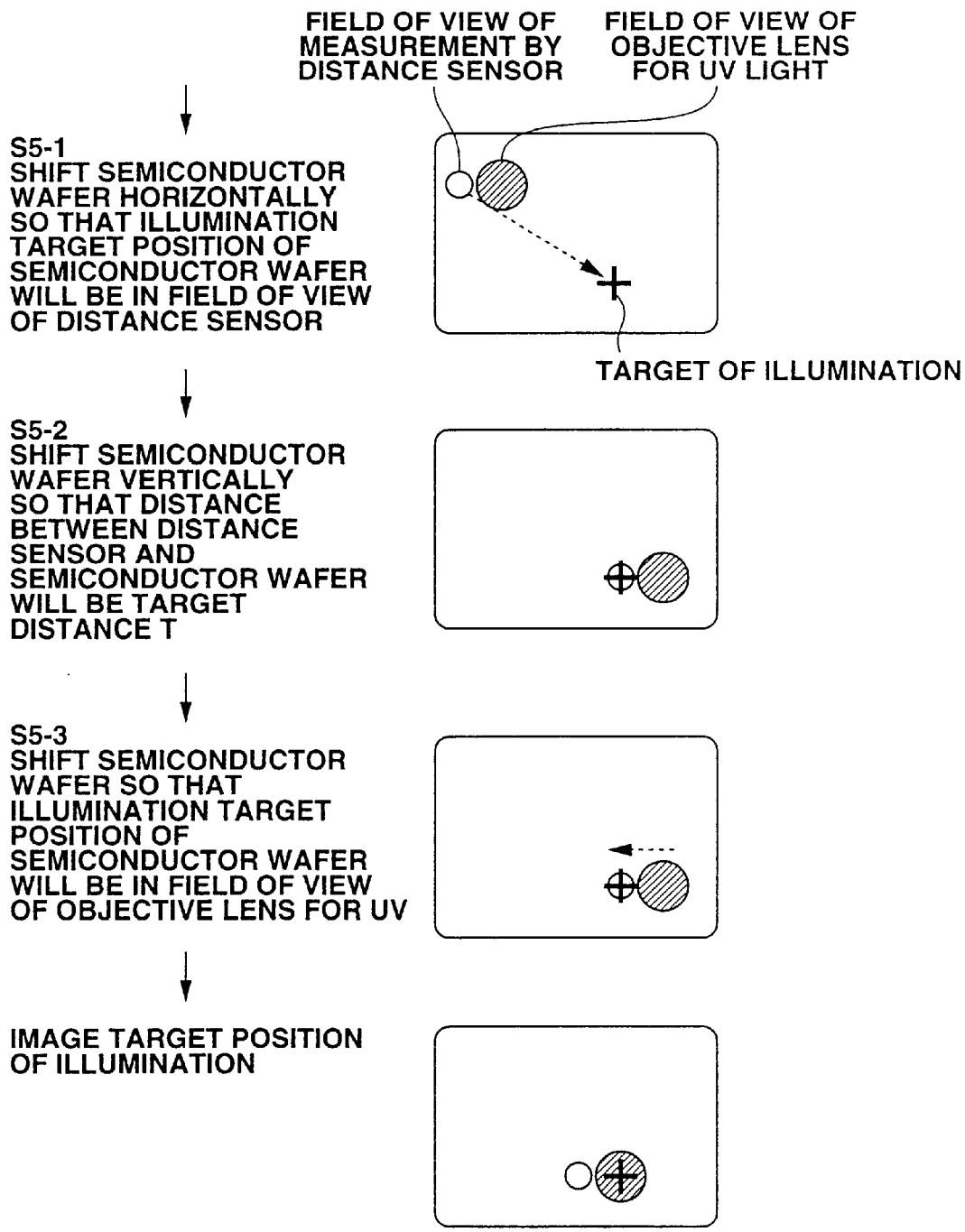
FIG. 14 is a flowchart for illustrating the operational sequence of the movement operation of the objective lens for UV light to a coordinate of an object of measurement and auto-focussing operation in inspecting the semiconductor wafer by the inspection device according to the present invention.

In the inspection process for the semiconductor wafer, explained in connection with the flowchart of FIGS. 9 to 12, the operation of shifting to the coordinate to be measured and of auto-focussing of the steps S5-1 to S5-3 of FIG. 14 is carried out on both the defect image (steps S1-11, S2-12, S3-2 and S4-2) and on the reference image (steps S1-14, S2-15, S3-5 and S4-5). It is noted that, instead of carrying out the movement from the defect image coordinate to the reference image coordinate in two steps, the objective lens for UV light 40 on the defect image coordinate may directly be shifted to the reference image coordinate to effect auto-focussing of the reference image coordinate at this position.

In the foregoing description, the inspection device 1 according to the present invention is used for scrutinizing into the nature of the defect in the semiconductor wafer. However, the inspection device 1 of the present invention may also be used for other purposes than defect discrimination on the semiconductor wafer. That is, the inspection device 1 of the present invention may also be used for inspecting whether or not a device pattern formed on the semiconductor wafer is formed to a proper shape in meeting with the desired pattern. The usage of the inspection device 1 according to the present invention is not limited to inspection of the semiconductor wafer. That is, the inspection device 1 of the present invention can be broadly applied to inspection of fine patterns, for example, to inspection of a flat panel display carrying a fie pattern.

What is claimed is:

1. A focal anoint position control mechanism for UV light comprising:
supporting means for supporting an object of illumination;
UV light illuminating means for illuminating UV light, converged by an objective lens, onto the object of illumination carried by said supporting means;

distance detection means mounted at a fixed position with respect to the objective lens for detecting the distance to said object of illumination; and position control means for shifting said supporting means and/or the objective lens for controlling the relative position between said object of illumination and the objective lens;

said position control means controlling the distance between said object of illumination and the object lens to a pre-set target distance based on the distance detected by said distance detection means, wherein, said position control means shifts said object of illumination and the objective lens relatively to each other to set the objective lens at a position coincident with the illumination target point of said object of illumination, and said position control means causing said distance detection means to detect the distance to said object of illumination to control the distance between the object of illumination and the objective lens to a pre-set target distance based on the distance as detected by said distance detection means.

2. A focal point position control mechanism for UV light comprising:

supporting means for supporting an object of illumination;

UV light illuminating means for illuminating UV light, converged by an objective lens, onto the object of illumination carried by said supporting means;

distance detection means mounted at a fixed position with respect to the objective lens for detecting the distance to said object of illumination; and position control means for shifting said supporting means and/or the objective lens for controlling the relative position between said object of illumination and the objective lens;

said position control means controlling the distance between said object of illumination and the object lens to a pre-set target distance based on the distance detected by said distance detection means, wherein, said position control means shifts said object of illumination and the objective lens relatively to each other to set the distance detection means at a position coincident with the illumination target point of said object of illumination; and said position control means causing said distance detection means to detect the distance to said object of illumination to cause relative movement between the object of illumination and the objective lens to set the objective lens at a position coincident with the illumination target point of said object of illumination;

said position control means controlling the distance between the object of illumination and the objective lens to a pre-set target distance based on the distance as detected by said distance detection means.

3. A focal point position control mechanism for UV light comprising:

supporting means for supporting an object of illumination;

UV light illuminating means for illuminating UV light, converged by an objective lens, onto the object of illumination carried by said supporting means;

distance detection means mounted at a fixed position with respect to the objective lens for detecting the distance to said object of illumination; and position control means for shifting said Supporting means and/or the objective lens for controlling the relative position between said object of illumination and the objective lens;

said position control means controlling the distance between said object of illumination and the object lens to a pre-set target distance based on the distance detected by said distance detection means, wherein, said position control means corrects the pre-set target distance based on a first correction value as set in keeping with respective positions on a movement coordinate when said object of illumination is parallel to said objective lens.

4. A focal point position control mechanism for UV light comprising:

supporting means for supporting an object of illumination;

UV light illuminating means for illuminating UV light, converged by an objective lens, onto the object of illumination carried by said supporting means;

distance detection means mounted at a fixed position with respect to the objective lens for detecting the distance to said object of illumination; and position control means for shifting said supporting means and/or the objective lens for controlling the relative position between said object of illumination and the objective lens;

said position control means controlling the distance between said object of illumination and the object lens to a pre-set target distance based on the distance detected by said distance detection means, wherein, said position control means corrects the pre-set target distance based on a second correction value as set in keeping with each illumination position on said object of illumination.

5. A focal point position control mechanism for UV light comprising:

supporting means for supporting an object of illumination;

UV light illuminating means for illuminating UV light, converged by an objective lens, onto the object of illumination carried by said supporting means;

distance detection means mounted at a fixed position with respect to the objective lens for detecting the distance to said object of illumination; and position control means for shifting said supporting means and/or the objective lens for controlling the relative position between said object of illumination and the objective lens;

said position control means controlling the distance between said object of illumination and the object lens to a pre-set target distance based on the distance detected by said distance detection means, wherein, said position control means corrects the distance as detected by said distance detection means based on a third correction value as set responsive to a drift accompanying temporal changes of the distance as detected by said distance detection means.

6. A focal point position mechanism for UV light comprising:

supporting means for supporting an object of illumination;

UV light illuminating means for illuminating UV light, converged by an objective lens, onto the object of illumination carried by said supporting means;

distance detection means mounted at a fixed position with respect to the objective lens for detecting the distance to said object of illumination; and position control means for shifting said supporting means and/or the objective lens for controlling the relative position between said object of illumination and the objective lens;

said position control means controlling the distance between said object of illumination and the object lens to a pre-set target distance based on the distance detected by said distance detection means, wherein, said position control means corrects the pre-set target distance based on a first correction value as set in keeping with respective positions on a movement coordinate when said object of illumination is parallel to said objective lens and on a second correction value as set in keeping with each illumination position on said object of illumination; and said position control means also correcting the distance detected by said distance detection means based on a third correction value as set responsive to a drift accompanying temporal changes of the distance as detected by said distance detection means.

7. A focal point position control mechanism for UV light comprising:

supporting means for supporting an object of illumination;

UV light illuminating means for illuminating UV light, converged by an objective lens, onto the object of illumination carried by said supporting means;

distance detection means mounted at a fixed position with respect to the objective lens for detecting the distance to said object of illumination; and position control means for shifting said supporting means and/or the objective lens for controlling the relative position between said object of illumination and the objective lens;

said position control means controlling the distance between said object of illumination and the object lens to a pre-set target distance based on tile distance detected by said distance detection means, wherein, said distance detection means is a capacitance type sensor.

8. A focal point position control mechanism for UV light comprising:

supporting means for supporting an object of illumination;

UV light illuminating means for illuminating UV light, converged by an objective lens, onto the object of illumination carried by said supporting means:

distance detection means mounted at a fixed position with respect to the objective lens for detecting the distance to said object of illumination; and position control means for shifting said supporting means and/or the objective lens for controlling the relative position between said object of illumination and the objective lens;

said position control means controlling the distance between said object of illumination and the object lens to a pre-set target distance based on the distance detected by said distance detection means, wherein, said distance detection means is formed integrally with said objective lens.

9. A method for controlling the focal point position of the UV light, in which the focal point position of the UV light converged by an objective lens is brought into coincidence with an optional position of the object of illumination, comprising:

detecting a distance up to said object of illumination by a distance detection device having a fixed relative position with respect to said objective lens, and controlling the distance between the object of illumination and the objective lens to a pre-set target distance based on a distance as detected by said distance detection device, wherein, said object of illumination and the objective lens are translated until said objective lens is at a position coincident with an illumination target point of said object of illumination; the distance to said object of illumination is detected by said distance detection device; and the distance between said object of illumination and the objective lens is controlled to a pre-set target distance based on the distance as detected by said distance detection device.

10. A method for controlling the focal point position of the UV light, in which the focal point position of the UV light converged by an objective lens is brought into coincidence with an optional position of the object of illumination, comprising:

detecting a distance up to said object of illumination by a distance detection device having a fixed relative position with respect to said objective lens, and controlling the distance between the object of illumination and the objective lens to a pre-set target distance based on a distance as detected by said distance detection device, wherein, said object of illumination and the objective lens are translated until said distance detection device is at a position coincident with an illumination target point of said object of illumination;

the distance to said object of illumination is detected by said distance detection device;

said object of illumination and the objective lens are translated until said objective lens is at a position coincident with an illumination target point of said object of illumination; and the distance between said object of illumination and the objective lens is controlled to a pre-set target distance based on the distance as detected by said distance detection device.

11. A method for controlling the focal point position of the UV light in which the focal point position of the UV light converged by an objective lens is brought into coincidence with an optional position of the object of illumination, comprising;

detecting a distance up to said object of illumination by a distance detection device having a fixed relative position with respect to said objective lens, and controlling the distance between the object of illumination and the objective lens to a pre-set target distance based on a distance as detected by said distance detection device, wherein,
said pre-set target distance is corrected based on a first correction value as set in association with each position on the movement coordinate when said object of illumination is parallel to said objective lens.

12. A method for controlling the focal point position of the UV light, in which the focal point position of the UV light converged by an objective lens is brought into coincidence with an optional position of the object of illumination, comprising:

detecting a distance up to said object of illumination by a distance detection device having a fixed relative position with respect to said objective lens, and controlling the distance between the object of illumination and the objective lens to a pre-set target distance based on a distance as detected by said distance detection device, wherein, said pre-set target distance is corrected based on a second correction value as set in keeping with each illumination position on said object of illumination.

13. A method for controlling the focal point position of the UV light, in which the focal point position of the UV light converged by an objective lens is brought into coincidence with an optional position of the object of illumination, comprising:

detecting a distance up to said object of illumination by a distance detection device having a fixed relative position with respect to said objective lens, and controlling the distance between the object of illumination and the objective lens to a pre-set target distance based on a distance as detected by said distance detection device, wherein, the distance as detected by said distance detection device is corrected based on a third correction value as set in keeping with drift accompanying temporal changes of the distance as detected by said distance detection device.

14. A method for controlling the focal point position of the UV light, in which the focal point position of the UV light converged by an objective lens is brought into coincidence with an optional position of the object of illumination, comprising:

detecting a distance up to said object of illumination by a distance detection device having a fixed relative position with respect to said objective lens, and controlling the distance between the object of illumination and the objective lens to a pre-set target distance based on a distance as detected by said distance detection device, wherein, said pre-set target distance is corrected based on a first correction value as set in keeping with each position on the coordinate of movement when said object of illumination is parallel to the objective lens and on a second correction value as set in keeping with each illuminating position on said object of illumination; and the distance as detected by said distance detection device is corrected based on a third correction value as set in keeping with a drift accompanying temporal changes of the distance as detected by said distance detection device.

15. A method for controlling the focal point position of the UV light, in which the focal point position of the UV light converged by an objective lens is brought into coincidence with an optional position of the object of illumination, comprising:

detecting a distance up to said object of illumination by a distance detection device having a fixed relative position with respect to said objective lens, and controlling the distance between the object of illumination and the objective lens to a pre-set target distance based on a distance as detected by said distance detection device, wherein, the distance up to said object of illumination is detected by a distance detection device employing a capacitance type sensor.

16. A method for controlling the focal point position of the UV light, in which the focal point position of the UV light converged by an objective lens is brought into coincidence with an optional position of the object of illumination, comprising:

detecting a distance up to said object of illumination by a distance detection device having a fixed relative position with respect to said objective lens, and controlling the distance between the object of illumination and the objective lens to a pre-set target distance based on a distance as detected by said distance detection device, wherein, the distance up to said object of illumination is detected by a distance detection device formed integrally with said objective lens.

17. An inspection apparatus comprising:

supporting means for supporting an device;

UV light illuminating means for illuminating UV light, converged by an objective lens, onto the device carried by said supporting means;

distance detection means mounted at a fixed position with respect to said objective lens for detecting the distance to said device;

position control means for shifting said supporting means and/or the objective lens for controlling the relative position between said device and the objective lens;

UV light photographing means for detecting the reflected UV light illuminated on said device for photographing an image of said device; and inspection means for processing the image as photographed by said UV light photographing means for inspecting said device, wherein, said position control means controlling the distance between said device and the objective lens to a pre-set target distance based on the distance detected by said distance detection means.

18. The inspection apparatus according to claim 17:

wherein, said position control means shifts said device and the objective lens relatively to each other to set the objective lens at a position coincident with the illumination target point of said device; and said position control means causing said distance detection means to detect the distance to said device to control the distance between the device and the objective lens to a pre-set target distance based on the distance as detected by said distance detection means.

19. The inspection apparatus according to claim 17:

wherein, said position control means shifts said device and the objective lens relatively to each other to set the distance detection means at a position coincident with the illumination target point of said device;

said position control means causing said distance detection means to detect the distance to said device to cause relative movement between the device and the objective lens to set the objective lens at a position coincident with the illumination target point of said device;

said position control means controlling the distance between the device and the objective lens to a pre-set target distance based on the distance as detected by said distance detection means.

20. The inspection apparatus according to claim 17:

wherein, said position control means corrects the pre-set target distance based on a first correction value set in keeping with respective positions on a movement coordinate when said device is parallel to said objective lens.

21. The inspection apparatus according to claim 17, wherein, said position control means corrects the pre-set target distance based on a second correction value as set in keeping with each illumination position on said device.

22. The inspection apparatus according to claim 17, wherein, said position control means corrects the distance as detected by said distance detection means based on a third correction value as set responsive to a drift accompanying temporal changes of the distance as detected by said distance detection means.

23. The inspection apparatus according to claim 17, wherein, said position control means corrects the pre-set target distance based on a first correction value set in keeping with respective positions on a movement coordinate when said device is parallel to said objective lens and on a second correction value as set in keeping with each illumination position on said device; and said position control means also correcting the distance detected by said distance detection means based on a third correction value as set responsive to a drift accompanying temporal changes of the distance as detected by said distance detection means.

24. The inspection apparatus according to claim 17, wherein, said distance detection means is a capacitance type sensor.

25. The inspection apparatus according to claim 17, wherein, said distance detection means is formed integrally with said objective lens.

26. An inspection method in which the UV light converged by an objective lens is illuminated on a device to detect the reflected light to inspect said device, comprising:

detecting the distance to said device by a distance detection device mounted at a fixed position relative to said objective lens;

controlling the distance between said device and the objective lens to a pre-set target distance based on the distance as detected by said distance detection device;

illuminating the UV light converged by said objective lens;

detecting the reflected light of the UV light illuminated on said device to photograph an image of said device; and processing the image of said device as photographed for inspecting said device.

27. The inspection method according to claim 26, wherein, said device and the objective lens are translated to shift said objective lens to a position coincident with an illumination target point of said device;

the distance to said device is detected by said distance detection device; and the distance between the device and the objective lens is controlled to a pre-set target distance based on the distance as detected by said distance detection device.

28. The inspection method according to claim 26, wherein, said device and the objective lens are translated to shift said distance detection device to a position coincident with an illumination target point of said device;

the distance to said device is detected by said distance detection device;

said device and the objective lens are translated to shift the objective lens to a position coincident with the illumination target point of said device; and the distance between the device and the objective lens is controlled to a pre-set target distance based on the distance as detected by said distance detection device.

29. The inspection method according to claim 26, wherein, said pre-set target distance is corrected based on a first correction value set in keeping with respective positions on a movement coordinate when said device is parallel to said objective lens.

30. The inspection method according to claim 26, wherein, said pre-set target distance is corrected based on a second correction value as set in keeping with each illumination position on said device.

31. The inspection method according to claim 26, wherein, the distance as detected by said distance detection device is corrected based on a third correction value as set responsive to a drift accompanying temporal changes of the distance as detected by said distance detection device.

32. The inspection method according to claim 26, wherein, the pre-set target distance is corrected based on a first correction value as set in keeping with respective positions on a movement coordinate when said device is parallel to said objective lens and on a second correction value as set in keeping with each illumination position on said device; and the distance detected by said distance detection device is corrected based on a third correction value as set responsive to a drift accompanying temporal chances of the distance as detected by said distance detection device.

33. The inspection method according to claim 26, wherein, the distance up to said device is detected by a distance detection device employing a capacitance type sensor.

34. The inspection method according to claim 26, wherein, the distance to said device is detected by a distance detection device formed integrally with said objective lens.

* * * * *